United States Patent
Mesiwala et al.

(10) Patent No.: US 10,959,758 B2
(45) Date of Patent: Mar. 30, 2021

(54) IMPLANTS FOR SPINAL FIXATION OR FUSION

(71) Applicant: SI-Bone Inc., Santa Clara, CA (US)

(72) Inventors: Ali H. Mesiwala, Pomona, CA (US); Mark A. Reiley, Washington, DC (US); Paul Sand, Redwood City, CA (US); Bret W. Schneider, Morgan Hill, CA (US); Scott A. Yerby, Montara, CA (US)

(73) Assignee: SI-Bone Inc., Santa Clara, CA (US)

( * ) Notice: Subject to any disclaimer, the term of this patent is extended or adjusted under 35 U.S.C. 154(b) by 0 days.

(21) Appl. No.: 15/903,410

(22) Filed: Feb. 23, 2018

(65) Prior Publication Data

US 2018/0177534 A1    Jun. 28, 2018

Related U.S. Application Data

(62) Division of application No. 14/216,863, filed on Mar. 17, 2014, now Pat. No. 9,936,983.

(60) Provisional application No. 61/793,803, filed on Mar. 15, 2013.

(51) Int. Cl.
  *A61B 17/70* (2006.01)
  *A61B 17/84* (2006.01)

(52) U.S. Cl.
  CPC .......... *A61B 17/7055* (2013.01); *A61B 17/70* (2013.01); *A61B 17/846* (2013.01)

(58) Field of Classification Search
  CPC ............ A61B 17/7037; A61B 17/7035; A61B 17/7055; A61B 17/846; A61B 2017/8655
  See application file for complete search history.

(56) References Cited

U.S. PATENT DOCUMENTS

| | | | |
|---|---|---|---|
| 1,951,278 | A | 3/1934 | Ericsson |
| 2,136,471 | A | 11/1938 | Schneider |
| 2,243,717 | A | 5/1941 | Moreira |
| 2,414,882 | A | 7/1947 | Longfellow |
| 2,562,419 | A | 7/1951 | Ferris |

(Continued)

FOREIGN PATENT DOCUMENTS

| | | |
|---|---|---|
| CN | 1128944 A | 8/1996 |
| CN | 1190882 A | 8/1998 |

(Continued)

OTHER PUBLICATIONS

Acumed; Acutrak Headless Compressioin Screw (product information); 12 pgs; © 2005; retrieved Sep. 25, 2014 from http://www.rcsed.ac.uk/fellows/Ivanrensburg/classification/surgtech/acumed/manuals/acutrak-brochure%200311.pdf.

(Continued)

*Primary Examiner* — Julianna N Harvey
(74) *Attorney, Agent, or Firm* — Shay Glenn LLP; Thomas M. Zlogar

(57) ABSTRACT

The present invention generally relates to bone implants. More specifically, the present invention relates to bone implants used for the fixation or fusion of the sacroiliac joint and/or the spine. For example, a system for fusing or stabilizing a plurality of bones is provided. The system includes an implant structure having stem portion and a head portion, the stem portion having a rectilinear cross sectional area. A tulip or saddle structure can be attached to the head portion, and a rod can be secured within the tulip or saddle structure.

20 Claims, 18 Drawing Sheets

(56) References Cited

U.S. PATENT DOCUMENTS

| | | |
|---|---|---|
| 2,675,801 A | 4/1954 | Bambara et al. |
| 2,697,433 A | 12/1954 | Zehnder |
| 3,076,453 A | 2/1963 | Tronzo |
| 3,506,982 A | 4/1970 | Steffee |
| 3,694,821 A | 10/1972 | Moritz |
| 3,709,218 A | 1/1973 | Halloran |
| 3,744,488 A | 7/1973 | Cox |
| 4,059,115 A | 11/1977 | Jumashev et al. |
| 4,156,943 A | 6/1979 | Collier |
| 4,292,964 A | 10/1981 | Ulrich |
| 4,341,206 A | 7/1982 | Perrett et al. |
| 4,344,190 A | 8/1982 | Lee et al. |
| 4,399,813 A | 8/1983 | Barber |
| 4,423,721 A | 1/1984 | Otte et al. |
| 4,475,545 A | 10/1984 | Ender |
| 4,501,269 A | 2/1985 | Bagby |
| 4,569,338 A | 2/1986 | Edwards |
| 4,612,918 A | 9/1986 | Slocum |
| 4,622,959 A | 11/1986 | Marcus |
| 4,630,601 A | 12/1986 | Harder et al. |
| 4,638,799 A | 1/1987 | Moore |
| 4,657,550 A | 4/1987 | Daher |
| 4,743,256 A | 5/1988 | Brantigan |
| 4,773,402 A | 9/1988 | Asher et al. |
| 4,787,378 A | 11/1988 | Sodhi |
| 4,790,303 A | 12/1988 | Steffee |
| 4,834,757 A | 5/1989 | Brantigan |
| 4,846,162 A | 7/1989 | Moehring |
| 4,877,019 A | 10/1989 | Vives |
| 4,878,915 A | 11/1989 | Brantigan |
| 4,898,186 A | 2/1990 | Ikada et al. |
| 4,904,261 A | 2/1990 | Dove et al. |
| 4,950,270 A | 8/1990 | Bowman et al. |
| 4,961,740 A | 10/1990 | Ray et al. |
| 4,969,888 A | 11/1990 | Scholten et al. |
| 4,981,481 A | 1/1991 | Kranz et al. |
| 5,034,011 A | 7/1991 | Howland |
| 5,034,013 A | 7/1991 | Kyle et al. |
| 5,035,697 A | 7/1991 | Frigg |
| 5,041,118 A | 8/1991 | Wasilewski |
| 5,053,035 A | 10/1991 | McLaren |
| 5,059,193 A | 10/1991 | Kuslich |
| 5,066,296 A | 11/1991 | Chapman et al. |
| 5,102,414 A | 4/1992 | Kirsch |
| 5,108,397 A | 4/1992 | White |
| 5,122,141 A | 6/1992 | Simpson et al. |
| 5,139,498 A | 8/1992 | Astudillo Ley |
| 5,139,500 A | 8/1992 | Schwartz |
| 5,147,367 A | 9/1992 | Ellis |
| 5,147,402 A | 9/1992 | Bohler et al. |
| 5,190,551 A | 3/1993 | Chin et al. |
| 5,197,961 A | 3/1993 | Castle |
| 5,242,444 A | 9/1993 | MacMillan |
| 5,298,254 A | 3/1994 | Prewett et al. |
| 5,334,205 A | 8/1994 | Cain |
| 5,380,325 A | 1/1995 | Lahille et al. |
| 5,390,683 A | 2/1995 | Pisharodi |
| 5,433,718 A | 7/1995 | Brinker |
| 5,443,466 A | 8/1995 | Shah |
| 5,458,638 A | 10/1995 | Kuslich et al. |
| 5,470,334 A | 11/1995 | Ross et al. |
| 5,480,402 A | 1/1996 | Kim |
| 5,569,249 A | 10/1996 | James et al. |
| 5,591,235 A | 1/1997 | Kuslich |
| 5,593,409 A | 1/1997 | Michelson |
| 5,607,424 A | 3/1997 | Tropiano |
| 5,609,635 A | 3/1997 | Michelson |
| 5,609,636 A | 3/1997 | Kohrs et al. |
| 5,626,616 A | 5/1997 | Speece |
| 5,643,264 A | 7/1997 | Sherman et al. |
| 5,645,599 A | 7/1997 | Samani |
| 5,658,337 A | 8/1997 | Kohrs et al. |
| 5,667,510 A | 9/1997 | Combs |
| 5,669,909 A | 9/1997 | Zdeblick et al. |
| 5,672,178 A | 9/1997 | Petersen |
| 5,683,391 A | 11/1997 | Boyd |
| 5,709,683 A | 1/1998 | Bagby |
| 5,713,904 A | 2/1998 | Errico et al. |
| 5,716,358 A | 2/1998 | Ochoa et al. |
| 5,725,581 A | 3/1998 | Brånemark |
| 5,743,912 A | 4/1998 | LaHille et al. |
| 5,759,035 A | 6/1998 | Ricci |
| 5,766,174 A | 6/1998 | Perry |
| 5,766,252 A | 6/1998 | Henry et al. |
| 5,766,261 A | 6/1998 | Neal et al. |
| 5,788,699 A | 8/1998 | Bobst et al. |
| 5,800,440 A | 9/1998 | Stead |
| 5,868,749 A | 2/1999 | Reed |
| 5,897,556 A | 4/1999 | Drewry et al. |
| 5,928,239 A | 7/1999 | Mirza |
| 5,941,885 A | 8/1999 | Jackson |
| 5,961,522 A | 10/1999 | Mehdizadeh |
| 5,961,554 A | 10/1999 | Janson et al. |
| 6,010,507 A | 1/2000 | Rudloff |
| 6,015,409 A | 1/2000 | Jackson |
| 6,053,916 A | 4/2000 | Moore |
| 6,056,749 A | 5/2000 | Kuslich |
| 6,066,175 A | 5/2000 | Henderson et al. |
| 6,086,589 A | 7/2000 | Kuslich et al. |
| 6,096,080 A | 8/2000 | Nicholson et al. |
| 6,120,292 A | 9/2000 | Buser et al. |
| 6,120,504 A | 9/2000 | Brumback et al. |
| 6,143,031 A | 11/2000 | Knothe et al. |
| 6,197,062 B1 | 3/2001 | Fenlin |
| 6,206,924 B1 | 3/2001 | Timm |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,264,657 B1 | 7/2001 | Urbahns et al. |
| 6,270,528 B1 | 8/2001 | McKay |
| 6,287,343 B1 | 9/2001 | Kuslich et al. |
| 6,302,885 B1 | 10/2001 | Essiger |
| 6,302,914 B1 | 10/2001 | Michelson |
| 6,306,140 B1 | 10/2001 | Siddiqui |
| 6,319,253 B1 | 11/2001 | Ackeret et al. |
| 6,406,498 B1 | 6/2002 | Tormala et al. |
| 6,409,768 B1 | 6/2002 | Tepic et al. |
| 6,451,020 B1 | 9/2002 | Zucherman et al. |
| 6,471,707 B1 | 10/2002 | Miller et al. |
| 6,485,518 B1 | 11/2002 | Cornwall et al. |
| 6,497,707 B1 | 12/2002 | Bowman et al. |
| 6,517,541 B1 | 2/2003 | Sesic |
| 6,520,969 B2 | 2/2003 | Lambrecht et al. |
| 6,524,314 B1 | 2/2003 | Dean et al. |
| 6,527,775 B1 | 3/2003 | Warburton |
| 6,556,857 B1 | 4/2003 | Estes et al. |
| 6,558,386 B1 | 5/2003 | Cragg |
| 6,565,566 B1 | 5/2003 | Wagner et al. |
| 6,575,899 B1 | 6/2003 | Foley et al. |
| 6,575,991 B1 | 6/2003 | Chesbrough et al. |
| 6,579,293 B1 | 6/2003 | Chandran |
| 6,582,431 B1 | 6/2003 | Ray |
| 6,582,467 B1 | 6/2003 | Teitelbaum et al. |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,607,530 B1 | 8/2003 | Carl et al. |
| 6,620,163 B1 | 9/2003 | Michelson |
| 6,635,059 B2 | 10/2003 | Randall et al. |
| 6,666,868 B2 | 12/2003 | Fallin |
| 6,669,529 B1 | 12/2003 | Scaries |
| 6,673,075 B2 | 1/2004 | Santilli |
| 6,692,501 B2 | 2/2004 | Michelson |
| 6,712,852 B1 | 3/2004 | Chung et al. |
| 6,723,099 B1 | 4/2004 | Goshert |
| 6,740,118 B2 | 5/2004 | Eisermann et al. |
| 6,743,257 B2 | 6/2004 | Castro |
| D493,533 S | 7/2004 | Blain |
| 6,793,656 B1 | 9/2004 | Mathews |
| 6,827,740 B1 | 12/2004 | Michelson |
| 6,984,235 B2 | 1/2006 | Huebner |
| 6,989,033 B1 | 1/2006 | Schmidt |

(56) References Cited

U.S. PATENT DOCUMENTS

| | | |
|---|---|---|
| 6,991,461 B2 | 1/2006 | Gittleman |
| 7,118,579 B2 | 10/2006 | Michelson |
| 7,147,666 B1 | 12/2006 | Grisoni |
| 7,175,663 B1 | 2/2007 | Stone |
| 7,211,085 B2 | 5/2007 | Michelson |
| 7,223,269 B2 | 5/2007 | Chappuis |
| 7,314,488 B2 | 1/2008 | Reiley |
| 7,335,205 B2 | 2/2008 | Aeschlimann et al. |
| 7,338,500 B2 | 3/2008 | Chappuis |
| 7,396,365 B2 | 7/2008 | Michelson |
| 7,452,359 B1 | 11/2008 | Michelson |
| 7,452,369 B2 | 11/2008 | Barry |
| 7,481,831 B2 | 1/2009 | Bonutti |
| 7,527,649 B1 | 5/2009 | Blain |
| 7,534,254 B1 | 5/2009 | Michelson |
| 7,537,616 B1 | 5/2009 | Branch et al. |
| 7,569,054 B2 | 8/2009 | Michelson |
| 7,569,059 B2 | 8/2009 | Cerundolo |
| 7,601,155 B2 | 10/2009 | Petersen |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,727,235 B2 | 6/2010 | Contiliano et al. |
| 7,758,646 B2 | 7/2010 | Khandkar et al. |
| 7,780,704 B2 | 8/2010 | Markworth et al. |
| 7,850,732 B2 | 12/2010 | Heinz |
| 7,857,832 B2 | 12/2010 | Culbert et al. |
| 7,887,565 B2 | 2/2011 | Michelson |
| 7,901,439 B2 | 3/2011 | Horton |
| 7,909,832 B2 | 3/2011 | Michelson |
| 7,922,765 B2 | 4/2011 | Reiley |
| 7,942,879 B2 | 5/2011 | Christie et al. |
| 8,052,728 B2 | 11/2011 | Hestad |
| 8,062,365 B2 | 11/2011 | Schwab |
| 8,066,705 B2 | 11/2011 | Michelson |
| 8,066,709 B2 | 11/2011 | Michelson |
| 8,142,481 B2 | 3/2012 | Warnick |
| 8,202,305 B2 | 6/2012 | Reiley |
| 8,308,779 B2 | 11/2012 | Reiley |
| 8,317,862 B2 | 11/2012 | Troger et al. |
| 8,348,950 B2 | 1/2013 | Assell et al. |
| 8,388,667 B2 | 3/2013 | Reiley et al. |
| 8,394,129 B2 | 3/2013 | Morgenstern Lopez |
| 8,398,635 B2 | 3/2013 | Vaidya |
| 8,414,648 B2 | 4/2013 | Reiley |
| 8,425,570 B2 | 4/2013 | Reiley |
| 8,430,930 B2 | 4/2013 | Hunt |
| 8,444,693 B2 | 5/2013 | Reiley |
| 8,467,851 B2 | 6/2013 | Mire et al. |
| 8,470,004 B2 | 6/2013 | Reiley |
| 8,529,608 B2 | 9/2013 | Terrill et al. |
| 8,608,802 B2 | 12/2013 | Bagga et al. |
| D697,209 S | 1/2014 | Walthall et al. |
| 8,641,737 B2 | 2/2014 | Matthis et al. |
| 8,672,986 B2 | 3/2014 | Klaue et al. |
| 8,734,462 B2 | 5/2014 | Reiley et al. |
| 8,778,026 B2 | 7/2014 | Mauldin |
| 8,840,623 B2 | 9/2014 | Reiley |
| 8,840,651 B2 | 9/2014 | Reiley |
| 8,858,601 B2 | 10/2014 | Reiley |
| 8,920,477 B2 | 12/2014 | Reiley |
| 8,945,190 B2 | 2/2015 | Culbert et al. |
| 8,945,193 B2 | 2/2015 | Kirschman |
| 8,951,254 B2 | 2/2015 | Mayer et al. |
| 8,951,293 B2 | 2/2015 | Glazer et al. |
| 8,951,295 B2 | 2/2015 | Matityahu et al. |
| 8,961,571 B2 | 2/2015 | Lee et al. |
| 8,986,348 B2 | 3/2015 | Reiley |
| RE45,484 E | 4/2015 | Foley et al. |
| 9,039,743 B2 | 5/2015 | Reiley |
| 9,044,321 B2 | 6/2015 | Mauldin et al. |
| 9,131,955 B2 | 9/2015 | Swofford |
| 9,149,286 B1 | 10/2015 | Greenhalgh et al. |
| 9,198,676 B2 | 12/2015 | Pilgeram et al. |
| 9,220,535 B2 | 12/2015 | Röbling et al. |
| 9,375,243 B1 | 6/2016 | Vestgaarden |
| 9,375,323 B2 | 6/2016 | Reiley |
| 9,451,999 B2 | 9/2016 | Simpson et al. |
| 9,452,065 B1 | 9/2016 | Lawson |
| 9,486,264 B2 | 11/2016 | Reiley et al. |
| 9,492,201 B2 | 11/2016 | Reiley |
| 9,498,264 B2 | 11/2016 | Harshman et al. |
| 9,510,872 B2 | 12/2016 | Donner et al. |
| 9,517,095 B2 | 12/2016 | Vaidya |
| 9,526,548 B2 | 12/2016 | Asfora |
| 9,554,909 B2 | 1/2017 | Donner |
| 9,561,063 B2 | 2/2017 | Reiley |
| 9,566,100 B2 | 2/2017 | Asfora |
| 9,603,613 B2 | 3/2017 | Schoenefeld et al. |
| 9,615,856 B2 | 4/2017 | Arnett et al. |
| 9,622,783 B2 | 4/2017 | Reiley et al. |
| 9,636,226 B2 | 5/2017 | Hunt |
| 9,662,124 B2 | 5/2017 | Assell et al. |
| 9,662,128 B2 | 5/2017 | Reiley |
| 9,662,157 B2 | 5/2017 | Schneider et al. |
| 9,662,158 B2 | 5/2017 | Reiley |
| 9,675,394 B2 | 6/2017 | Reiley |
| 9,743,969 B2 | 8/2017 | Reiley |
| 9,757,154 B2 | 9/2017 | Donner et al. |
| 9,820,789 B2 | 11/2017 | Reiley |
| 9,839,448 B2 | 12/2017 | Reckling et al. |
| 9,936,983 B2 | 4/2018 | Mesiwala et al. |
| 9,949,843 B2 | 4/2018 | Reiley et al. |
| 9,956,013 B2 | 5/2018 | Reiley et al. |
| 10,219,885 B2 | 3/2019 | Mamo et al. |
| 10,799,367 B2 | 10/2020 | Vrionis et al. |
| 2001/0012942 A1 | 8/2001 | Estes et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0019637 A1 | 2/2002 | Frey et al. |
| 2002/0029043 A1 | 3/2002 | Ahrens et al. |
| 2002/0038123 A1 | 3/2002 | Visotsky et al. |
| 2002/0049497 A1 | 4/2002 | Mason |
| 2002/0077641 A1 | 6/2002 | Michelson |
| 2002/0082598 A1 | 6/2002 | Teitelbaum |
| 2002/0120275 A1 | 8/2002 | Schmieding et al. |
| 2002/0128652 A1 | 9/2002 | Ferree |
| 2002/0143334 A1 | 10/2002 | von Hoffmann et al. |
| 2002/0143335 A1 | 10/2002 | von Hoffmann et al. |
| 2002/0151903 A1 | 10/2002 | Takei et al. |
| 2002/0169507 A1 | 11/2002 | Malone |
| 2002/0183858 A1 | 12/2002 | Contiliano et al. |
| 2002/0198527 A1 | 12/2002 | Mockter |
| 2003/0018336 A1 | 1/2003 | Vandewalle |
| 2003/0032961 A1 | 2/2003 | Pelo et al. |
| 2003/0050642 A1 | 3/2003 | Schmieding et al. |
| 2003/0065332 A1 | 4/2003 | TenHuisen et al. |
| 2003/0074000 A1 | 4/2003 | Roth et al. |
| 2003/0078660 A1 | 4/2003 | Clifford et al. |
| 2003/0083668 A1 | 5/2003 | Rogers et al. |
| 2003/0083688 A1 | 5/2003 | Simonson |
| 2003/0097131 A1 | 5/2003 | Schon et al. |
| 2003/0139815 A1 | 7/2003 | Grooms et al. |
| 2003/0181979 A1 | 9/2003 | Ferree |
| 2003/0181982 A1 | 9/2003 | Kuslich |
| 2003/0199983 A1 | 10/2003 | Michelson |
| 2003/0229358 A1 | 12/2003 | Errico et al. |
| 2003/0233146 A1 | 12/2003 | Grinberg et al. |
| 2003/0233147 A1 | 12/2003 | Nicholson et al. |
| 2004/0010315 A1 | 1/2004 | Song |
| 2004/0024458 A1 | 2/2004 | Senegas et al. |
| 2004/0034422 A1 | 2/2004 | Errico et al. |
| 2004/0073216 A1 | 4/2004 | Lieberman |
| 2004/0073314 A1 | 4/2004 | White et al. |
| 2004/0082955 A1 | 4/2004 | Zirkle |
| 2004/0087948 A1 | 5/2004 | Suddaby |
| 2004/0097927 A1 | 5/2004 | Yeung et al. |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0138750 A1 | 7/2004 | Mitchell |
| 2004/0138753 A1 | 7/2004 | Ferree |

(56) References Cited

U.S. PATENT DOCUMENTS

| | | |
|---|---|---|
| 2004/0147929 A1 | 7/2004 | Biedermann et al. |
| 2004/0158324 A1 | 8/2004 | Lange |
| 2004/0176287 A1 | 9/2004 | Harrison et al. |
| 2004/0176853 A1 | 9/2004 | Sennett et al. |
| 2004/0181282 A1 | 9/2004 | Zucherman et al. |
| 2004/0186572 A1 | 9/2004 | Lange et al. |
| 2004/0210221 A1 | 10/2004 | Kozak et al. |
| 2004/0225360 A1 | 11/2004 | Malone |
| 2004/0230305 A1 | 11/2004 | Gorensek et al. |
| 2004/0260286 A1 | 12/2004 | Ferree |
| 2004/0267369 A1 | 12/2004 | Lyons et al. |
| 2005/0015059 A1 | 1/2005 | Sweeney |
| 2005/0015146 A1 | 1/2005 | Louis et al. |
| 2005/0033435 A1 | 2/2005 | Belliard et al. |
| 2005/0049590 A1 | 3/2005 | Alleyne et al. |
| 2005/0055023 A1 | 3/2005 | Sohngen et al. |
| 2005/0075641 A1 | 4/2005 | Singhatat et al. |
| 2005/0080415 A1 | 4/2005 | Keyer et al. |
| 2005/0107878 A1 | 5/2005 | Conchy |
| 2005/0112397 A1 | 5/2005 | Rolfe et al. |
| 2005/0124993 A1 | 6/2005 | Chappuis |
| 2005/0131409 A1* | 6/2005 | Chervitz ............ A61F 2/30771 606/247 |
| 2005/0137605 A1 | 6/2005 | Assell et al. |
| 2005/0143837 A1 | 6/2005 | Ferree |
| 2005/0149192 A1 | 7/2005 | Zucherman et al. |
| 2005/0159749 A1 | 7/2005 | Levy et al. |
| 2005/0165398 A1 | 7/2005 | Reiley |
| 2005/0192572 A1 | 9/2005 | Abdelgany et al. |
| 2005/0228384 A1 | 10/2005 | Zucherman et al. |
| 2005/0246021 A1 | 11/2005 | Ringeisen et al. |
| 2005/0251146 A1 | 11/2005 | Martz et al. |
| 2005/0273101 A1* | 12/2005 | Schumacher ...... A61B 17/7037 606/306 |
| 2005/0277940 A1 | 12/2005 | Neff |
| 2006/0036247 A1 | 2/2006 | Michelson |
| 2006/0036251 A1 | 2/2006 | Reiley |
| 2006/0036252 A1 | 2/2006 | Baynham et al. |
| 2006/0036322 A1* | 2/2006 | Reiley .................. A61F 2/4455 623/17.11 |
| 2006/0054171 A1 | 3/2006 | Dall |
| 2006/0058793 A1 | 3/2006 | Michelson |
| 2006/0058800 A1 | 3/2006 | Ainsworth et al. |
| 2006/0062825 A1 | 3/2006 | Maccecchini |
| 2006/0084986 A1 | 4/2006 | Grinberg et al. |
| 2006/0089656 A1 | 4/2006 | Allard et al. |
| 2006/0111779 A1 | 5/2006 | Petersen |
| 2006/0129247 A1 | 6/2006 | Brown et al. |
| 2006/0142772 A1 | 6/2006 | Ralph et al. |
| 2006/0161163 A1 | 7/2006 | Shino |
| 2006/0178673 A1 | 8/2006 | Curran |
| 2006/0195094 A1 | 8/2006 | McGraw et al. |
| 2006/0217717 A1* | 9/2006 | Whipple .............. A61B 17/686 606/278 |
| 2006/0241776 A1 | 10/2006 | Brown et al. |
| 2006/0271054 A1 | 11/2006 | Sucec et al. |
| 2006/0293662 A1 | 12/2006 | Boyer, II et al. |
| 2007/0027544 A1 | 2/2007 | McCord et al. |
| 2007/0038219 A1 | 2/2007 | Matthis et al. |
| 2007/0049933 A1 | 3/2007 | Ahn et al. |
| 2007/0066977 A1 | 3/2007 | Assell et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0093898 A1 | 4/2007 | Schwab et al. |
| 2007/0106383 A1* | 5/2007 | Abdou .................. A61B 17/70 623/17.11 |
| 2007/0149976 A1 | 6/2007 | Hale et al. |
| 2007/0156144 A1 | 7/2007 | Ulrich et al. |
| 2007/0156241 A1 | 7/2007 | Reiley et al. |
| 2007/0156246 A1 | 7/2007 | Meswania et al. |
| 2007/0161989 A1 | 7/2007 | Heinz et al. |
| 2007/0173820 A1 | 7/2007 | Trieu |
| 2007/0219634 A1 | 9/2007 | Greenhalgh et al. |
| 2007/0233146 A1 | 10/2007 | Henniges et al. |
| 2007/0233247 A1 | 10/2007 | Schwab |
| 2007/0250166 A1 | 10/2007 | McKay |
| 2007/0270879 A1 | 11/2007 | Isaza et al. |
| 2007/0282443 A1 | 12/2007 | Globerman et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0021480 A1 | 1/2008 | Chin et al. |
| 2008/0065093 A1 | 3/2008 | Assell et al. |
| 2008/0065215 A1 | 3/2008 | Reiley |
| 2008/0071356 A1 | 3/2008 | Greenhalgh et al. |
| 2008/0109083 A1 | 5/2008 | Van Hoeck et al. |
| 2008/0132901 A1 | 6/2008 | Recoules-Arche et al. |
| 2008/0140082 A1 | 6/2008 | Erdem et al. |
| 2008/0147079 A1 | 6/2008 | Chin et al. |
| 2008/0154374 A1 | 6/2008 | Labrom |
| 2008/0161810 A1 | 7/2008 | Melkent |
| 2008/0183204 A1 | 7/2008 | Greenhalgh et al. |
| 2008/0234758 A1 | 9/2008 | Fisher et al. |
| 2008/0255562 A1 | 10/2008 | Gil et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0306554 A1 | 12/2008 | McKinley |
| 2009/0012529 A1 | 1/2009 | Blain et al. |
| 2009/0018660 A1 | 1/2009 | Roush |
| 2009/0024174 A1 | 1/2009 | Stark |
| 2009/0036927 A1 | 2/2009 | Vestgaarden |
| 2009/0037148 A1 | 2/2009 | Lin et al. |
| 2009/0043393 A1 | 2/2009 | Duggal et al. |
| 2009/0082810 A1* | 3/2009 | Bhatnagar .......... A61B 17/7044 606/250 |
| 2009/0082869 A1 | 3/2009 | Slemker et al. |
| 2009/0099602 A1 | 4/2009 | Aflatoon |
| 2009/0099610 A1 | 4/2009 | Johnson et al. |
| 2009/0105770 A1 | 4/2009 | Berrevoets et al. |
| 2009/0118771 A1 | 5/2009 | Gonzalez-Hernandez |
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0187247 A1 | 7/2009 | Metcalf, Jr. et al. |
| 2009/0216238 A1 | 8/2009 | Stark |
| 2009/0270929 A1 | 10/2009 | Suddaby |
| 2009/0287254 A1 | 11/2009 | Nayet et al. |
| 2009/0312798 A1 | 12/2009 | Varela |
| 2009/0324678 A1 | 12/2009 | Thorne et al. |
| 2010/0022535 A1 | 1/2010 | Lee et al. |
| 2010/0076502 A1 | 3/2010 | Guyer et al. |
| 2010/0081107 A1 | 4/2010 | Bagambisa et al. |
| 2010/0094290 A1 | 4/2010 | Vaidya |
| 2010/0094295 A1 | 4/2010 | Schnieders et al. |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0131011 A1 | 5/2010 | Stark |
| 2010/0137990 A1 | 6/2010 | Apatsidis et al. |
| 2010/0145461 A1 | 6/2010 | Landry et al. |
| 2010/0160977 A1 | 6/2010 | Gephart et al. |
| 2010/0168798 A1 | 7/2010 | Clineff et al. |
| 2010/0191292 A1 | 7/2010 | DeMeo et al. |
| 2010/0268228 A1 | 10/2010 | Petersen |
| 2010/0280619 A1 | 11/2010 | Yuan et al. |
| 2010/0280622 A1 | 11/2010 | McKinley |
| 2010/0286778 A1 | 11/2010 | Eisermann et al. |
| 2010/0331851 A1 | 12/2010 | Huene |
| 2010/0331893 A1 | 12/2010 | Geist et al. |
| 2011/0009869 A1 | 1/2011 | Marino et al. |
| 2011/0022089 A1 | 1/2011 | Assell et al. |
| 2011/0029019 A1 | 2/2011 | Ainsworth et al. |
| 2011/0040362 A1 | 2/2011 | Godara et al. |
| 2011/0046737 A1 | 2/2011 | Teisen |
| 2011/0060373 A1 | 3/2011 | Russell et al. |

(56) References Cited

U.S. PATENT DOCUMENTS

| | | |
|---|---|---|
| 2011/0060375 A1 | 3/2011 | Bonutti |
| 2011/0066190 A1 | 3/2011 | Schaller et al. |
| 2011/0082551 A1 | 4/2011 | Kraus |
| 2011/0093020 A1 | 4/2011 | Wu |
| 2011/0098747 A1* | 4/2011 | Donner ............... A61B 17/70 606/264 |
| 2011/0098816 A1 | 4/2011 | Jacob et al. |
| 2011/0098817 A1 | 4/2011 | Eckhardt et al. |
| 2011/0106175 A1 | 5/2011 | Rezach |
| 2011/0153018 A1 | 6/2011 | Walters et al. |
| 2011/0160866 A1 | 6/2011 | Laurence et al. |
| 2011/0178561 A1 | 7/2011 | Roh |
| 2011/0184518 A1 | 7/2011 | Trieu |
| 2011/0184519 A1 | 7/2011 | Trieu |
| 2011/0184520 A1 | 7/2011 | Trieu |
| 2011/0196372 A1 | 8/2011 | Murase |
| 2011/0230966 A1 | 9/2011 | Trieu |
| 2011/0238074 A1 | 9/2011 | Ek |
| 2011/0238181 A1 | 9/2011 | Trieu |
| 2011/0245930 A1 | 10/2011 | Alley et al. |
| 2011/0257755 A1 | 10/2011 | Bellemere et al. |
| 2011/0264229 A1 | 10/2011 | Donner |
| 2011/0295272 A1 | 12/2011 | Assell et al. |
| 2011/0295370 A1 | 12/2011 | Suh et al. |
| 2011/0313532 A1 | 12/2011 | Hunt |
| 2011/0319995 A1 | 12/2011 | Voellmicke et al. |
| 2012/0004730 A1 | 1/2012 | Castro |
| 2012/0083887 A1 | 4/2012 | Purcell et al. |
| 2012/0095560 A1 | 4/2012 | Donner |
| 2012/0179256 A1 | 7/2012 | Reiley |
| 2012/0191191 A1 | 7/2012 | Trieu |
| 2012/0226318 A1* | 9/2012 | Wenger ............... A61B 17/68 606/264 |
| 2012/0253398 A1 | 10/2012 | Metcalf et al. |
| 2012/0259372 A1 | 10/2012 | Glazer et al. |
| 2012/0271424 A1 | 10/2012 | Crawford |
| 2012/0277866 A1 | 11/2012 | Kalluri et al. |
| 2012/0296428 A1 | 11/2012 | Donner |
| 2012/0323285 A1 | 12/2012 | Assell et al. |
| 2013/0018427 A1 | 1/2013 | Pham et al. |
| 2013/0030456 A1 | 1/2013 | Assell et al. |
| 2013/0030529 A1 | 1/2013 | Hunt |
| 2013/0035727 A1 | 2/2013 | Datta |
| 2013/0053852 A1 | 2/2013 | Greenhalgh et al. |
| 2013/0053854 A1 | 2/2013 | Schoenefeld et al. |
| 2013/0053902 A1 | 2/2013 | Trudeau |
| 2013/0053963 A1 | 2/2013 | Davenport |
| 2013/0085535 A1 | 4/2013 | Greenhalgh et al. |
| 2013/0096683 A1 | 4/2013 | Kube |
| 2013/0116793 A1 | 5/2013 | Kloss |
| 2013/0123850 A1 | 5/2013 | Schoenefeld et al. |
| 2013/0123935 A1 | 5/2013 | Hunt et al. |
| 2013/0131678 A1 | 5/2013 | Dahners |
| 2013/0144343 A1 | 6/2013 | Arnett et al. |
| 2013/0158609 A1 | 6/2013 | Mikhail et al. |
| 2013/0172736 A1 | 7/2013 | Abdou |
| 2013/0197590 A1 | 8/2013 | Assell et al. |
| 2013/0203088 A1 | 8/2013 | Baerlecken et al. |
| 2013/0218215 A1 | 8/2013 | Ginn et al. |
| 2013/0218282 A1 | 8/2013 | Hunt |
| 2013/0231746 A1 | 9/2013 | Ginn et al. |
| 2013/0237988 A1 | 9/2013 | Mauldin |
| 2013/0245703 A1 | 9/2013 | Warren et al. |
| 2013/0245763 A1 | 9/2013 | Mauldin |
| 2013/0267836 A1 | 10/2013 | Mauldin et al. |
| 2013/0267961 A1 | 10/2013 | Mauldin et al. |
| 2013/0267989 A1 | 10/2013 | Mauldin et al. |
| 2013/0274890 A1 | 10/2013 | McKay |
| 2013/0296953 A1 | 11/2013 | Mauldin et al. |
| 2013/0325129 A1 | 12/2013 | Huang |
| 2014/0012340 A1 | 1/2014 | Beck et al. |
| 2014/0031934 A1 | 1/2014 | Trieu |
| 2014/0031935 A1 | 1/2014 | Donner et al. |
| 2014/0031938 A1 | 1/2014 | Lechmann et al. |
| 2014/0031939 A1 | 1/2014 | Wolfe et al. |
| 2014/0046380 A1 | 2/2014 | Asfora |
| 2014/0074175 A1 | 3/2014 | Ehler et al. |
| 2014/0088596 A1 | 3/2014 | Assell et al. |
| 2014/0088707 A1 | 3/2014 | Donner et al. |
| 2014/0121776 A1 | 5/2014 | Hunt |
| 2014/0135927 A1 | 5/2014 | Pavlov et al. |
| 2014/0142700 A1 | 5/2014 | Donner et al. |
| 2014/0172027 A1* | 6/2014 | Biedermann ........ A61B 17/866 606/326 |
| 2014/0200618 A1 | 7/2014 | Donner et al. |
| 2014/0207240 A1 | 7/2014 | Stoffman et al. |
| 2014/0257294 A1 | 9/2014 | Gedet et al. |
| 2014/0257408 A1 | 9/2014 | Trieu et al. |
| 2014/0276846 A1 | 9/2014 | Mauldin et al. |
| 2014/0276851 A1 | 9/2014 | Schneider et al. |
| 2014/0277139 A1 | 9/2014 | Vrionis et al. |
| 2014/0277165 A1 | 9/2014 | Katzman et al. |
| 2014/0277460 A1 | 9/2014 | Schifano et al. |
| 2014/0277462 A1 | 9/2014 | Yerby et al. |
| 2014/0277463 A1 | 9/2014 | Yerby et al. |
| 2014/0288649 A1 | 9/2014 | Hunt |
| 2014/0288650 A1 | 9/2014 | Hunt |
| 2014/0296982 A1 | 10/2014 | Cheng |
| 2014/0330382 A1 | 11/2014 | Mauldin |
| 2014/0364917 A1 | 12/2014 | Sandstrom et al. |
| 2015/0012051 A1 | 1/2015 | Warren et al. |
| 2015/0039037 A1 | 2/2015 | Donner et al. |
| 2015/0080072 A1 | 3/2015 | Chin et al. |
| 2015/0080951 A1 | 3/2015 | Yeh |
| 2015/0094765 A1 | 4/2015 | Donner et al. |
| 2015/0112444 A1 | 4/2015 | Aksu |
| 2015/0147397 A1 | 5/2015 | Altschuler |
| 2015/0150683 A1 | 6/2015 | Donner et al. |
| 2015/0173805 A1 | 6/2015 | Donner et al. |
| 2015/0173904 A1 | 6/2015 | Stark |
| 2015/0182268 A1 | 7/2015 | Donner et al. |
| 2015/0190149 A1 | 7/2015 | Assell et al. |
| 2015/0190187 A1 | 7/2015 | Parent et al. |
| 2015/0216566 A1 | 8/2015 | Mikhail et al. |
| 2015/0238203 A1 | 8/2015 | Asfora |
| 2015/0250513 A1 | 9/2015 | De Lavigne Sainte |
| 2015/0250595 A1 | 9/2015 | Mauldin et al. |
| 2015/0250611 A1 | 9/2015 | Schifano et al. |
| 2015/0250612 A1 | 9/2015 | Schifano et al. |
| 2015/0257892 A1 | 9/2015 | Lechmann et al. |
| 2015/0320469 A1 | 11/2015 | Biedermann et al. |
| 2016/0022429 A1 | 1/2016 | Greenhalgh et al. |
| 2016/0081810 A1 | 3/2016 | Reiley et al. |
| 2016/0095711 A1 | 4/2016 | Castro |
| 2016/0184103 A1 | 6/2016 | Fonte et al. |
| 2016/0242912 A1 | 8/2016 | Lindsey et al. |
| 2016/0249940 A1 | 9/2016 | Stark |
| 2016/0287171 A1 | 10/2016 | Sand et al. |
| 2016/0324643 A1 | 11/2016 | Donner et al. |
| 2016/0374727 A1 | 12/2016 | Greenhalgh et al. |
| 2017/0007409 A1 | 1/2017 | Mauldin et al. |
| 2017/0014235 A1 | 1/2017 | Jones et al. |
| 2017/0020585 A1 | 1/2017 | Harshman et al. |
| 2017/0049488 A1 | 2/2017 | Vestgaarden |
| 2017/0128214 A1 | 5/2017 | Mayer |
| 2017/0135733 A1 | 5/2017 | Donner et al. |
| 2017/0143513 A1 | 5/2017 | Sandstrom et al. |
| 2017/0209155 A1 | 7/2017 | Petersen |
| 2017/0273729 A1 | 9/2017 | Reiley |
| 2017/0296244 A1 | 10/2017 | Schneider et al. |
| 2018/0228621 A1 | 8/2018 | Reiley et al. |
| 2018/0368894 A1 | 12/2018 | Wieland et al. |
| 2019/0159818 A1 | 5/2019 | Schneider et al. |
| 2019/0159901 A1 | 5/2019 | Mauldin et al. |
| 2019/0298542 A1 | 10/2019 | Kloss |
| 2019/0343640 A1 | 11/2019 | Donner et al. |
| 2019/0343641 A1 | 11/2019 | Mauldin et al. |
| 2019/0343653 A1 | 11/2019 | McKay |
| 2020/0008817 A1 | 1/2020 | Reiley et al. |
| 2020/0008850 A1 | 1/2020 | Mauldin et al. |

(56) References Cited

U.S. PATENT DOCUMENTS

| | | |
|---|---|---|
| 2020/0246158 A1 | 8/2020 | Bergey |
| 2020/0268525 A1 | 8/2020 | Mesiwala et al. |

FOREIGN PATENT DOCUMENTS

| | | |
|---|---|---|
| CN | 1909848 A | 2/2007 |
| CN | 101795632 A | 8/2010 |
| CN | 102361601 A | 2/2012 |
| EP | 1287796 A1 | 3/2003 |
| JP | 59200642 A | 11/1984 |
| JP | 05-176942 A | 7/1993 |
| JP | 05184615 A | 7/1993 |
| JP | 09149906 A | 10/1997 |
| JP | 10-85231 A | 4/1998 |
| JP | 11318931 A | 11/1999 |
| JP | 2002509753 A | 4/2002 |
| JP | 2003511198 A | 3/2003 |
| JP | 2003533329 A | 11/2003 |
| JP | 2003534046 A | 11/2003 |
| JP | 2004121841 | 4/2004 |
| JP | 2004512895 | 4/2004 |
| JP | 2004516866 | 6/2004 |
| JP | 2006506181 | 2/2006 |
| JP | 2007535973 A | 12/2007 |
| JP | 2008540036 A | 11/2008 |
| JP | 2009521990 A | 6/2009 |
| JP | 2009533159 A | 9/2009 |
| JP | 2010137016 A | 6/2010 |
| JP | 2015510506 A | 4/2015 |
| WO | WO97/31517 A2 | 8/1997 |
| WO | WO01/17445 A1 | 3/2001 |
| WO | WO02/38054 | 5/2002 |
| WO | WO03/007839 A2 | 1/2003 |
| WO | WO04/02344 | 1/2004 |
| WO | WO2004/043277 A1 | 5/2004 |
| WO | WO2005/009729 A2 | 2/2005 |
| WO | WO2006/003316 | 1/2006 |
| WO | WO2006/023793 A2 | 3/2006 |
| WO | WO2009/029074 A1 | 3/2009 |
| WO | WO2010/105196 A1 | 9/2010 |
| WO | WO2011010463 A1 | 1/2011 |
| WO | WO2011/110865 A2 | 9/2011 |
| WO | WO2011/149557 A1 | 12/2011 |
| WO | WO2013/000071 A1 | 1/2013 |
| WO | WO2013/119907 A1 | 8/2013 |

OTHER PUBLICATIONS

Al-Khayer et al.; Percutaneous sacroiliac joint arthrodesis, a novel technique; J Spinal Disord Tech; vol. 21; No. 5; pp. 359-363; Jul. 2008.

Khurana et al.; Percutaneous fusion of the sacroiliac joint with hollow modular anchorage screws, clinical and radiological outcome; J Bone Joint Surg; vol. 91-B; No. 5; pp. 627-631; May 2009.

Lu et al.; Mechanical properties of porous materials; Journal of Porous Materials; 6(4); pp. 359-368; Nov. 1, 1999.

Peretz et al.; The internal bony architecture of the sacrum; Spine; 23(9); pp. 971-974; May 1, 1998.

Richards et al.; Bone density and cortical thickness in normal, osteopenic, and osteoporotic sacra; Journal of Osteoporosis; 2010(ID 504078); 5 pgs; Jun. 9, 2010.

Wise et al.; Minimally invasive sacroiliac arthrodesis, outcomes of a new technique; J Spinal Disord Tech; vol. 21; No. 8; pp. 579-584; Dec. 2008.

Reiley, Mark A.; U.S. Appl. No. 12/357,483 entitled "Systems and methods for the fixation or fusion of bone in the hand and wrist," filed Jan. 22, 2009 (abandoned).

Reckling et al.; U.S. Appl. No. 15/838,070 entitled "Implant placement," filed Dec. 11, 2017.

Sand et al.; U.S. Appl. No. 16/143,061 entitled "Systems and methods for decorticating the sacroiliac joint," filed Sep. 26, 2018.

Reiley et al.; U.S. Appl. No. 16/237,409 entitled "Implants for bone fixation or fusion," filed Dec. 31, 2018.

Mesiwala et al.; U.S. Appl. No. 16/276,430 entitled "Implants for spinal fixation and or fusion," filed Feb. 14, 2019.

Lindsey et al.; U.S. Appl. No. 16/368,686 entitled "Threaded implants and methods of use across bone segments," filed Mar. 28, 2019.

Reiley: U.S. Appl. No. 16/930;174 entitled Apparatus, system, and methods for the fixation or fusion of bone,: filed Jul. 15, 2020.

Reiley; U.S. Appl. No. 16/932,001 entitled "Apparatus, systems, and methods for the fixation or fusion of bone," filed Jul. 17, 2020.

Reiley; U.S. Appl. No. 16/933,084 entitled "Apparatus, systems, and methods for the fixation or fusion of bone," filed Jul. 20, 2020.

Reiley; U.S. Appl. No. 16/933,108 entitled "Apparatus, systems, and methods for the fixation or fusion of bone," filed Jul. 20, 2020.

\* cited by examiner

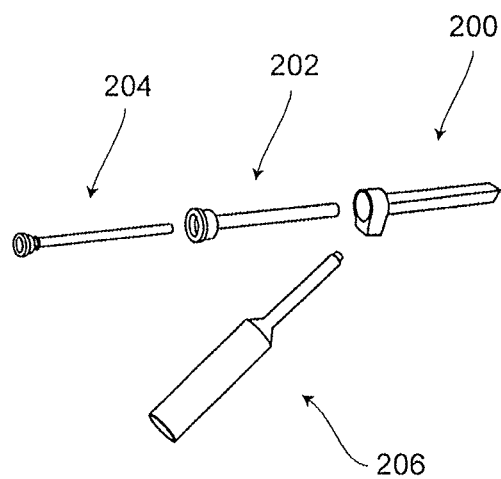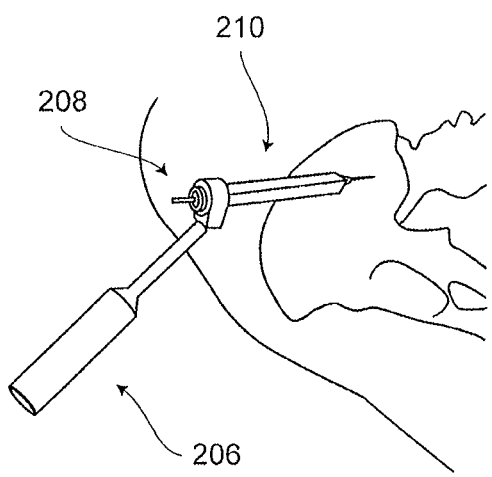
FIG. 2E
FIG. 2F

*(Anterior)*

*(Posterior)*

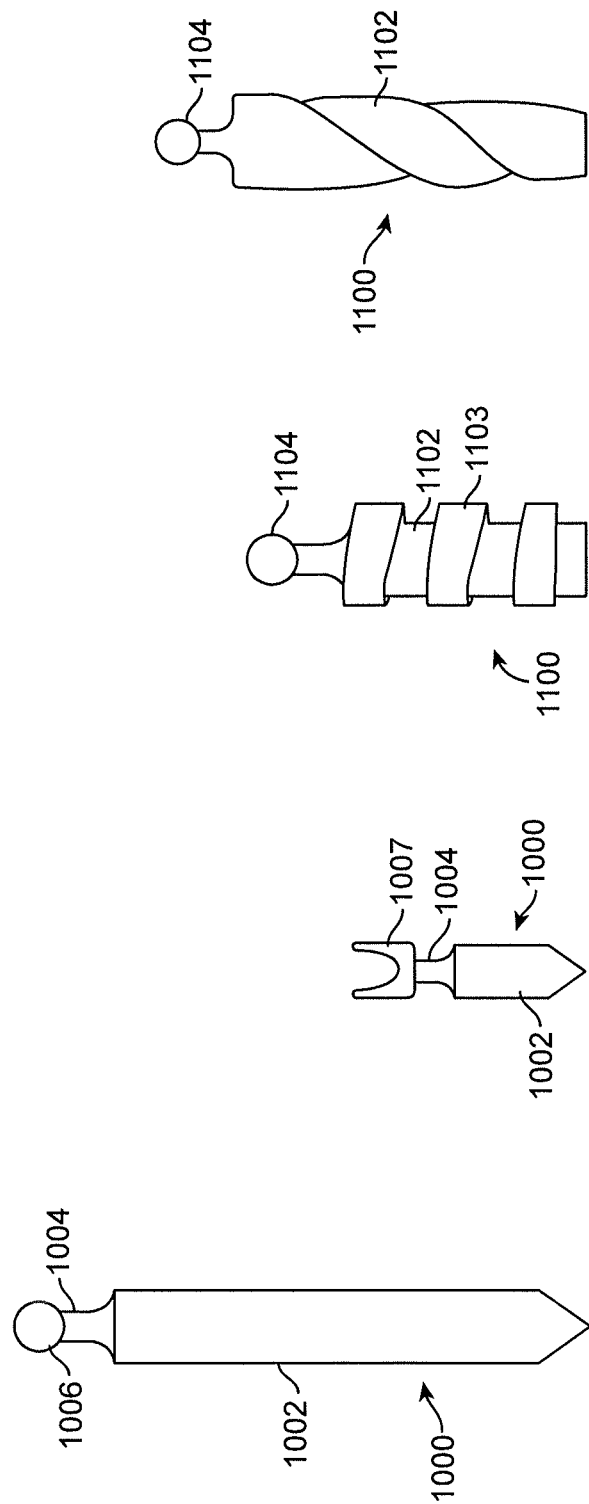

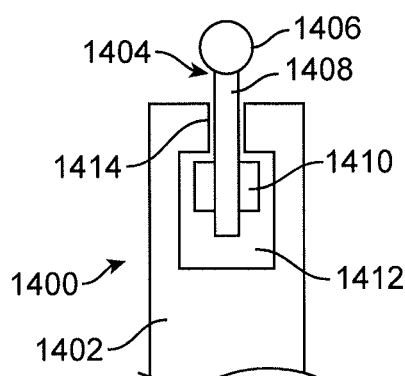
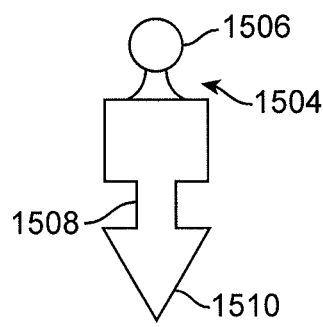
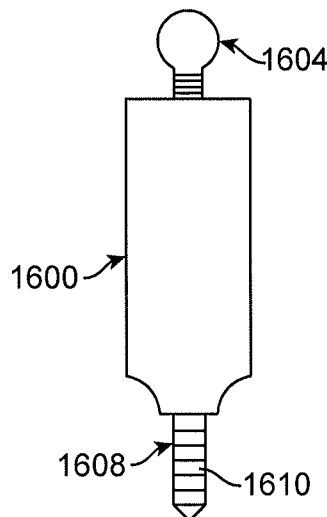
FIG. 14   FIG. 15   FIG. 16
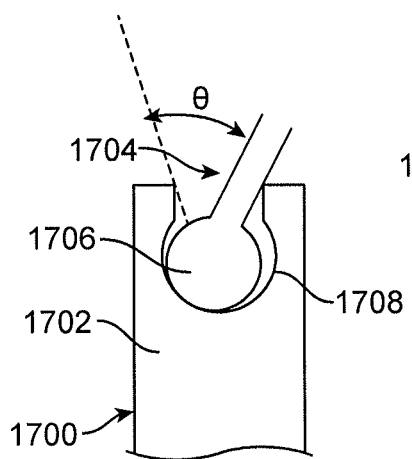
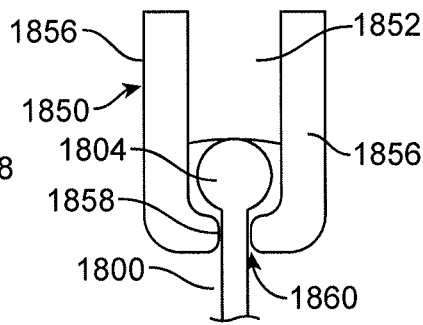
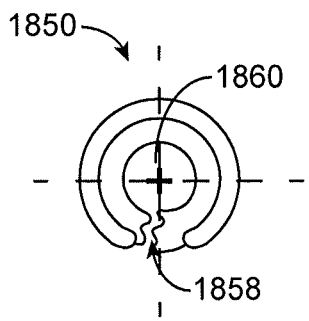
FIG. 17   FIG. 18A   FIG. 18B
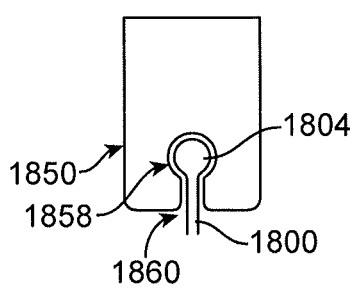
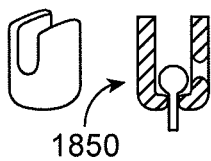
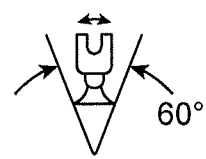
FIG. 18C   FIG. 18D   FIG. 18E Translaminar
Lumbar Fusion
(Posterior Approach)

IMPLANTS FOR SPINAL FIXATION OR FUSION

CROSS REFERENCE TO RELATED APPLICATIONS

This application is a divisional of U.S. application Ser. No. 14/216,863, filed Mar. 17, 2014, and titled "IMPLANTS FOR SPINAL FIXATION OR FUSION," which claims priority to U.S. Patent Provisional Application No. 61/793,803, filed Mar. 15, 2013, and titled "IMPLANTS FOR SPINAL FIXATION OR FUSION," each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference. For example, this application incorporates by reference in their entireties U.S. Patent Publication No. 2011/0087294, U.S. Patent Publication No. 2011/0087296, U.S. Patent Publication No. 2011/0118785, and U.S. Patent Publication No. 2011/0125268.

FIELD

The present invention generally relates to bone implants. More specifically, the present invention relates to bone implants used for the stabilization, fixation and/or fusion of the sacroiliac joint and/or the spine.

BACKGROUND

Many types of hardware are available both for the fixation of bones that are fractured and for the fixation of bones that are to be fused (arthrodesed).

For example, the human hip girdle is made up of three large bones joined by three relatively immobile joints. One of the bones is called the sacrum and it lies at the bottom of the lumbar spine, where it connects with the L5 vertebra. The other two bones are commonly called "hip bones" and are technically referred to as the right ilium and-the left ilium. The sacrum connects with both hip bones at the sacroiliac joint (in shorthand, the SI-Joint).

The SI-Joint functions in the transmission of forces from the spine to the lower extremities, and vice-versa. The SI-Joint has been described as a pain generator for up to 22% of lower back pain.

To relieve pain generated from the SI-Joint, sacroiliac joint fusion is typically indicated as surgical treatment, e.g., for degenerative sacroiliitis, inflammatory sacroiliitis, iatrogenic instability of the sacroiliac joint, osteitis condensans ilii, or traumatic fracture dislocation of the pelvis. Currently, screws and screws with plates are used for sacroiliac fusion. At the same time the cartilage has to be removed from the "synovial joint" portion of the SI-Joint. This requires a large incision to approach the damaged, subluxed, dislocated, fractured, or degenerative joint.

An alternative implant that is not based on the screw design can also be used to fuse the SI-Joint and/or the spine. Such an implant can have a triangular cross-section, for example, as further described below. To insert the implant, a cavity can be formed into the bone, and the implant can then be inserted into the cavity using a tool such as an impactor. The implants can then be stabilized together, if desired, by connecting the implants with a crossbar or other connecting device.

Therefore, it would be desirable to provide systems, devices and methods for SI-Joint and/or spinal stabilization, fixation and/or fusion.

SUMMARY OF THE DISCLOSURE

The present invention generally relates to bone implants. More specifically, the present invention relates to bone implants used for the stabilization, fixation or fusion of the sacroiliac joint and/or the spine.

In some embodiments, a system for fusing or stabilizing a plurality of bones is provided. The system includes an implant structure having stem portion and a head portion, the stem portion having a rectilinear cross sectional area. A tulip or saddle structure can be attached to the head portion, and a rod can be secured within the tulip or saddle structure.

In general, in one embodiment, a system for fusing or stabilizing a plurality of bones includes an implant structure having stem portion and a head portion, a tulip or saddle structure attached to the head portion, and a rod secured within the tulip or saddle structure. The stem portion has a rectilinear cross sectional area.

This and other embodiments can include one or more of the following features. The head portion can be connected to the stem portion with a Morse taper. The head portion can be connected to the stem portion with a screw attachment. The head portion can be integral with the stem portion. The tulip or saddle structure can include a first slot and a cavity for receiving the head portion. The tulip or saddle structure can be rotatable through a 60 degree range of motion.

In general, in one embodiment, an implant for spinal fixation or fusion includes an elongate body having a stem portion, a head portion, and a longitudinal axis. The stem portion has a rectilinear cross sectional area transverse to the longitudinal axis, and a tulip or saddle structure is attached to the head portion.

This and other embodiments can include one or more of the following features. The head portion can be connected to the stem portion with a Morse taper. The head portion can be connected to the stem portion with a screw attachment. The screw attachment can be formed on a shank that extends through the entire length of the elongate body. The head portion can be integral with the stem portion. The tulip or saddle structure can include a first slot and a cavity for receiving the head portion. The tulip or saddle structure can be rotatable through a 60 degree range of motion. The head portion can be connected to the stem portion through an expandable attachment on the head portion that is secured within a cavity in the stem portion. The tulip or saddle structure can be attached to the head portion through a snap on connection which can include a slot a receptacle in the tulip or saddle structure for receiving the head portion.

In general, in one embodiment, a method for stabilizing a first bone segment and a second bone segment of a patient includes implanting a first implant into the first bone segment. The first implant includes a stem portion configured to be inserted into the first bone segment and a tulip portion for receiving a rod. Implanting a second implant into the second bone segment includes a stem portion configured to be inserted into the second bone segment and a tulip portion for receiving the rod. The stem portion of the second implant has a rectilinear cross section transverse to a longitudinal axis of the stem portion of the second implant. The method further includes securing a rod to both the tulip portion of the first implant and the tulip portion of the second implant.

This and other embodiments can include one of more of the following features. The first implant can be a pedicle screw. The first implant can have a stem portion having a rectilinear cross section transverse to a longitudinal axis of the first implant. The first bone segment can be a vertebrae and the second bone segment can be the sacrum.

In general, in one embodiment, a method for pedicle screw salvage includes: (1) removing a pedicle screw from a bone segment to leave a cavity in the bone segment; and (2) inserting an implant into the cavity. The implant has a stem portion configured to be inserted into the bone segment and a tulip portion for receiving a rod. The stem portion has a rectilinear cross sectional profile transverse to a longitudinal axis of the stem portion.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 2E and 2F illustrate the assembly of a soft tissue protector system for placement over a guide wire.

FIGS. 5 to 7A and 7B are anatomic views showing, respectively, a pre-implanted perspective, implanted perspective, implanted anterior view, and implanted craniocaudal section view, the implantation of three implant structures for the fixation of the SI-Joint using a lateral approach through the ilium, the SI-Joint, and into the sacrum.

FIGS. 10A and 10B illustrate an embodiment of an implant structure with an integrated head portion.

FIGS. 11A and 11B illustrate embodiments of an implant structure suitable for pedicle screw salvage.

FIGS. 14 and 15 illustrate alternative embodiments of head portions with expandable attachment features.

FIG. 16 illustrates an embodiment of an implant structure with a screw-like head portion that extends completely through the stem portion of the implant structure.

FIG. 17 illustrates an embodiment of the attachment of the head portion to the stem portion of the implant structure using a ball and socket joint.

FIGS. 18A to 18E illustrate the head portion of the implant structure in connection with a tulip structure.

DETAILED DESCRIPTION

Figure 1:
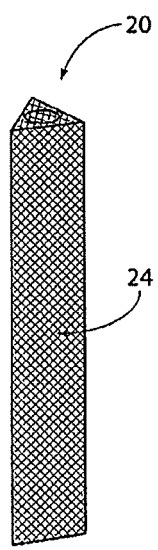
FIG. 1 illustrates an embodiment of an implant structure.
Figure 3:
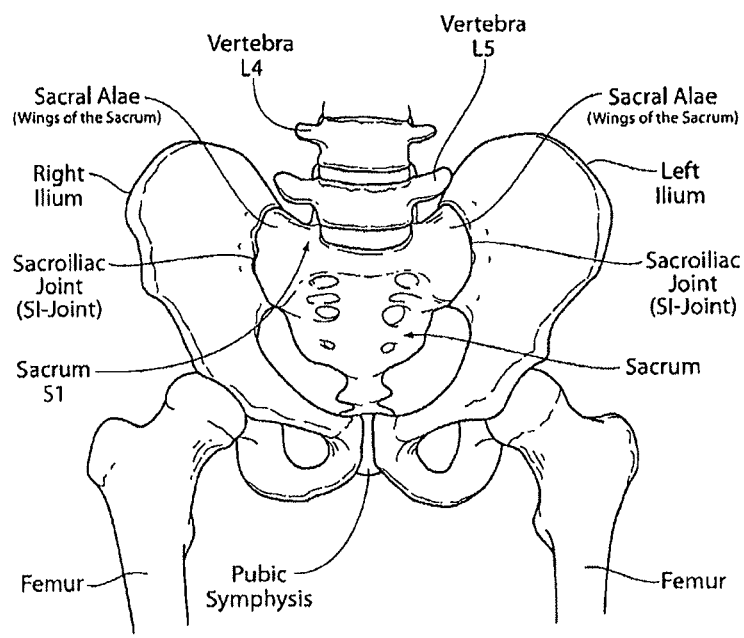
FIGS. 3 and 4 are, respectively, anterior and posterior anatomic views of the human hip girdle comprising the sacrum and the hip bones (the right ilium, and the left ilium), the sacrum being connected with both hip bones at the sacroiliac joint (in shorthand, the SI-Joint).
Figure 4:
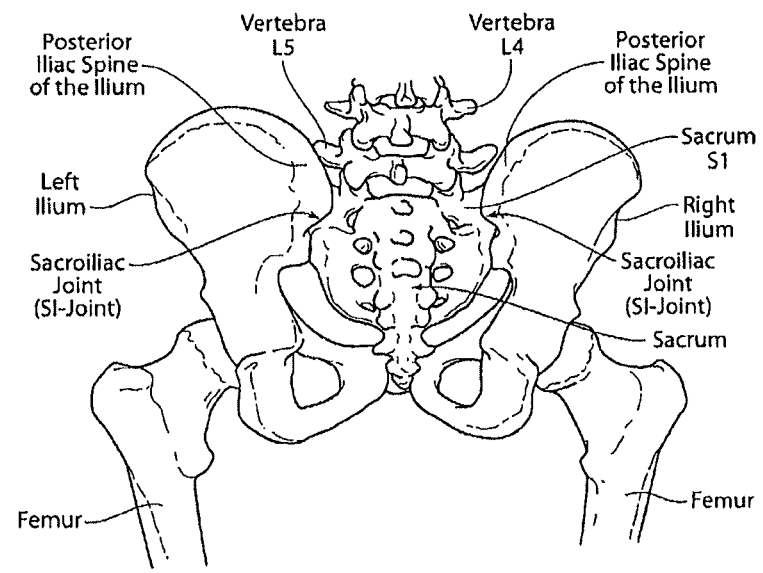

Elongated, stem-like implant structures 20 like that shown in FIG. 1 make possible the fixation of the SI-Joint (shown in anterior and posterior views, respectively, in FIGS. 3 and 4) in a minimally invasive manner. These implant structures 20 can be effectively implanted through the use a lateral surgical approach. The procedure is desirably aided by conventional lateral, inlet, and outlet visualization techniques, e.g., using X-ray image intensifiers such as a C-arms or fluoroscopes to produce a live image feed, which is displayed on a TV screen.

In one embodiment of a lateral approach (see FIGS. 5, 6, and 7A/B), one or more implant structures 20 are introduced laterally through the ilium, the SI-Joint, and into the sacrum. This path and resulting placement of the implant structures 20 are best shown in FIGS. 6 and 7A/B. In the illustrated embodiment, three implant structures 20 are placed in this manner. Also in the illustrated embodiment, the implant structures 20 are rectilinear in cross section and triangular in this case, but it should be appreciated that implant structures 20 of other rectilinear cross sections can be used.

Before undertaking a lateral implantation procedure, the physician identifies the SI-Joint segments that are to be fixated or fused (arthrodesed) using, e.g., the Fortin finger test, thigh thrust, FABER, Gaenslen's, compression, distraction, and diagnostic SI-Joint injection.

Figure 2A:
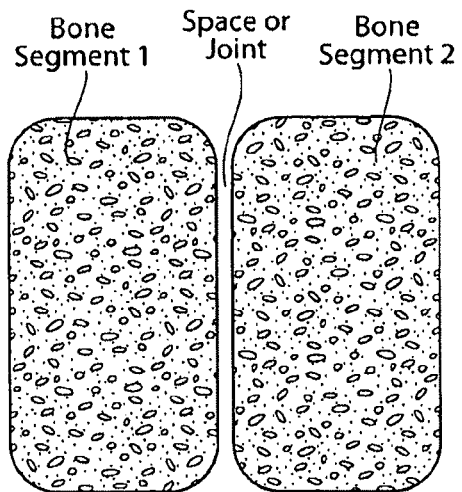
FIGS. 2A-2D are side section views of the formation of a broached bore in bone according to one embodiment of the invention.
Figure 2B:
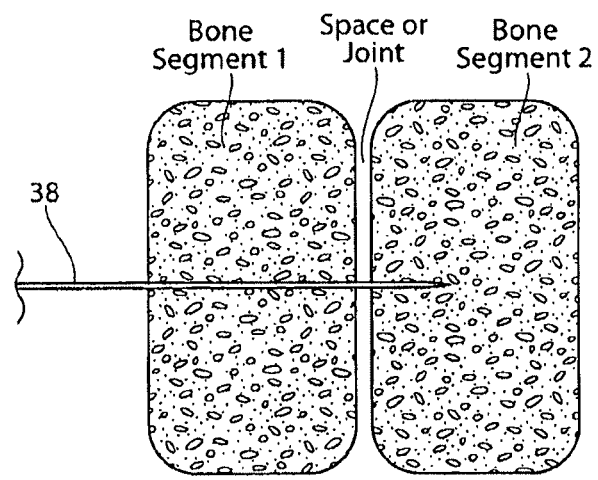

Aided by lateral, inlet, and outlet C-arm views, and with the patient lying in a prone position, the physician aligns the greater sciatic notches and then the alae (using lateral visualization) to provide a true lateral position. A 3 cm incision is made starting aligned with the posterior cortex of the sacral canal, followed by blunt tissue separation to the ilium. From the lateral view, the guide pin 38 (with sleeve (not shown)) (e.g., a Steinmann Pin) is started resting on the ilium at a position inferior to the sacrum end plate and just anterior to the sacral canal. In the outlet view, the guide pin 38 should be parallel to the sacrum end plate and in the inlet view the guide pin 38 should be at a shallow angle anterior (e.g., 15 .degree. to 20 .degree. off the floor, as FIG. 7B shows). In a lateral view, the guide pin 38 should be posterior to the sacrum anterior wall. In the outlet view, the guide pin 38 should be superior to the first sacral foramen and lateral of mid-line. This corresponds generally to the sequence shown diagrammatically in FIGS. 2A and 2B. A soft tissue protector (not shown) is desirably slipped over the guide pin 38 and firmly against the ilium before removing the guide pin sleeve (not shown).

Figure 2C:
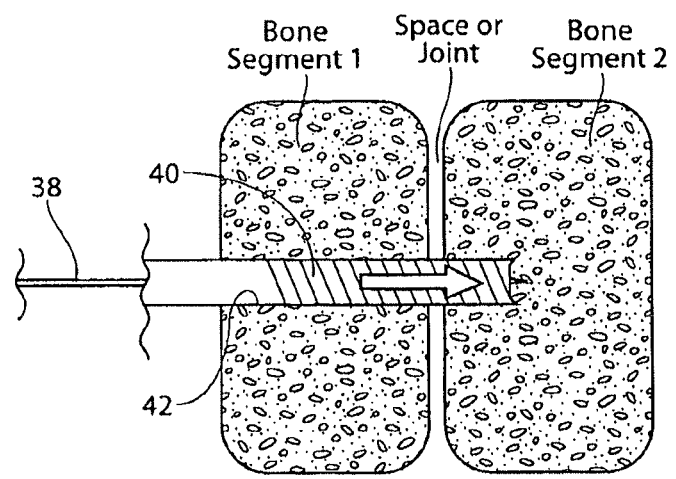

Over the guide pin 38 (and through the soft tissue protector), the pilot bore 42 is drilled in the manner previously described, as is diagrammatically shown in FIG. 2C. The pilot bore 42 extends through the ilium, through the SI-Joint, and into the Sl. The drill bit 40 is removed.

Figure 2D:
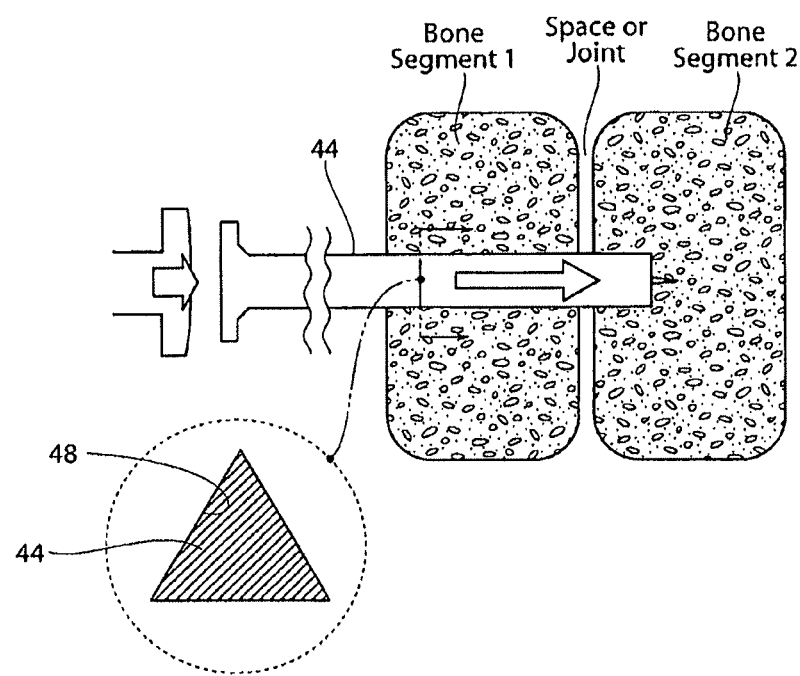

The shaped broach 44 is tapped into the pilot bore 42 over the guide pin 38 (and through the soft tissue protector) to create a broached bore 48 with the desired profile for the implant structure 20, which, in the illustrated embodiment, is triangular. This generally corresponds to the sequence shown diagrammatically in FIG. 2D. The triangular profile of the broached bore 48 is also shown in FIG. 5.

FIGS. 2E and 2F illustrate an embodiment of the assembly of a soft tissue protector or dilator or delivery sleeve 200 with a drill sleeve 202, a guide pin sleeve 204 and a handle 206. In some embodiments, the drill sleeve 202 and guide pin sleeve 204 can be inserted within the soft tissue protector 200 to form a soft tissue protector assembly 210 that can slide over the guide pin 208 until bony contact is achieved. The soft tissue protector 200 can be any one of the soft tissue protectors or dilators or delivery sleeves disclosed herein. In some embodiments, an expandable dilator or delivery sleeve 200 as disclosed herein can be used in place of a conventional soft tissue dilator. In the case of the expandable dilator, in some embodiments, the expandable dilator can be slid over the guide pin and then expanded before the drill sleeve 202 and/or guide pin sleeve 204 are inserted within the expandable dilator. In other embodiments, insertion of the drill sleeve 202 and/or guide pin sleeve 204 within the expandable dilator can be used to expand the expandable dilator.

In some embodiments, a dilator can be used to open a channel though the tissue prior to sliding the soft tissue protector assembly 210 over the guide pin. The dilator(s) can be placed over the guide pin, using for example a plurality of sequentially larger dilators or using an expandable dilator. After the channel has been formed through the tissue, the dilator(s) can be removed and the soft tissue protector assembly can be slid over the guide pin. In some embodiments, the expandable dilator can serve as a soft tissue protector after being expanded. For example, after expansion the drill sleeve and guide pin sleeve can be inserted into the expandable dilator.

Figure 5:
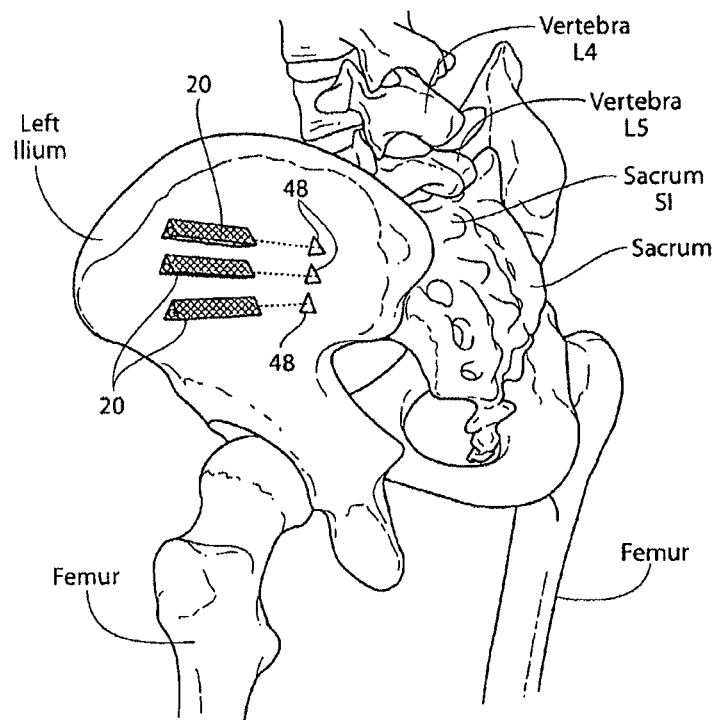
Figure 6:
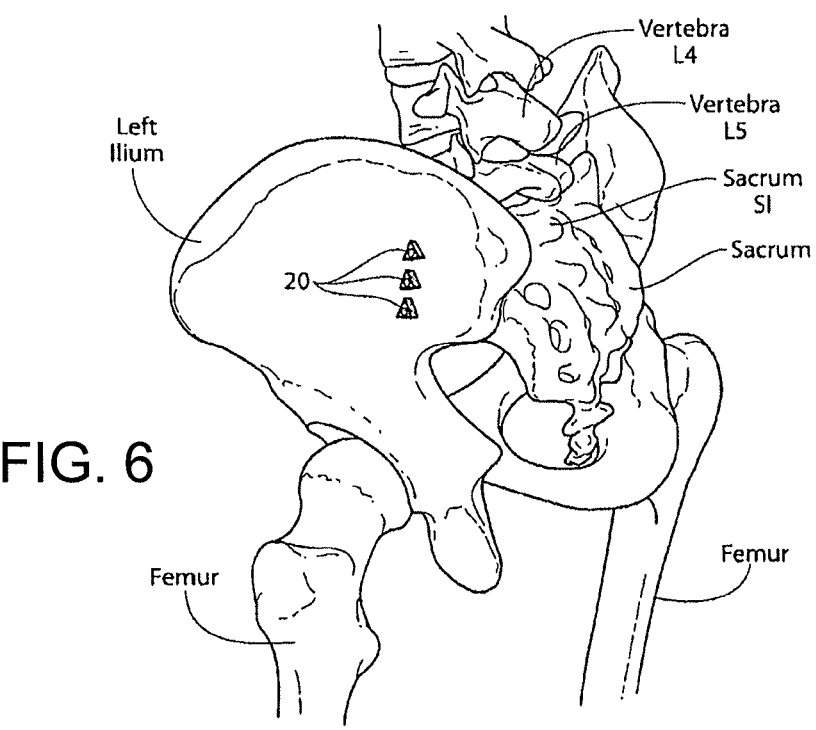
Figure 7A:
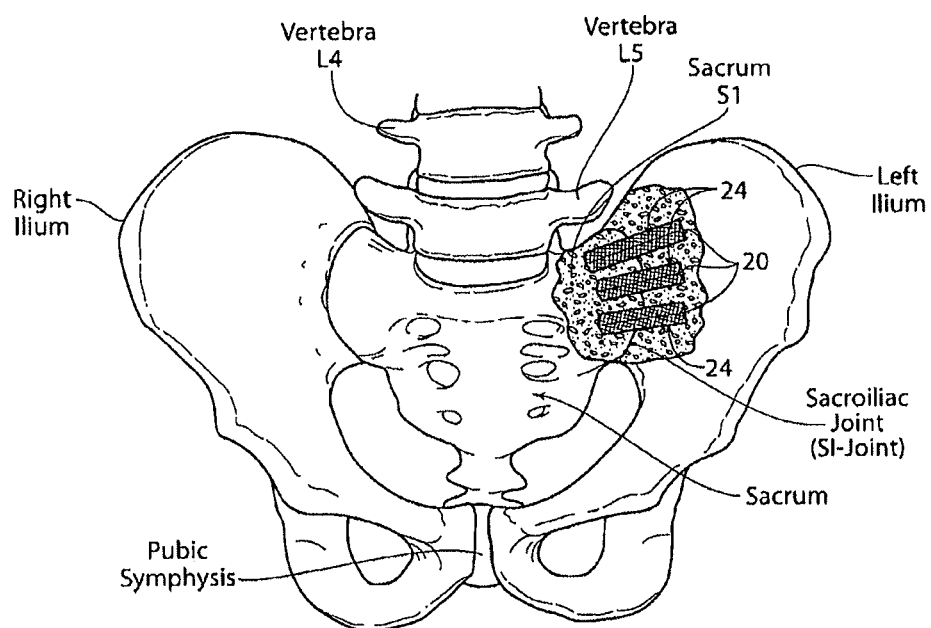
Figure 7B:
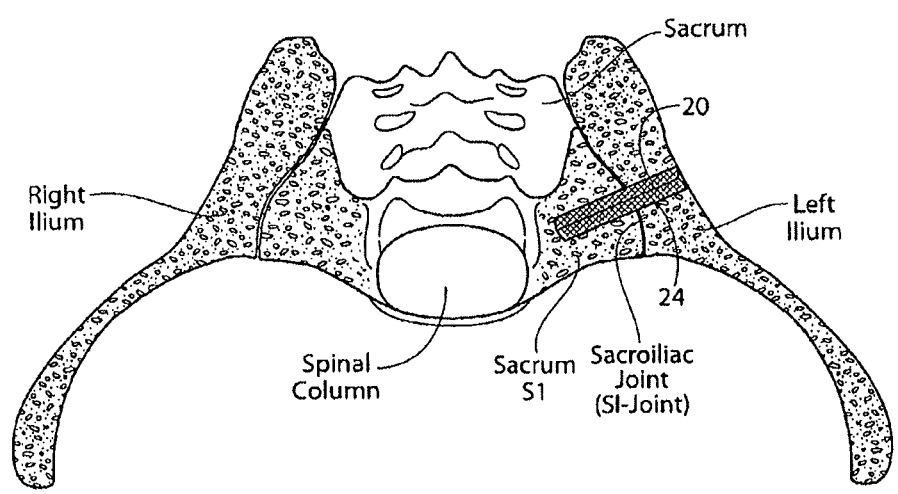

As shown in FIGS. 5 and 6, a triangular implant structure 20 can be now tapped through the soft tissue protector over the guide pin 38 through the ilium, across the SI-Joint, and into the sacrum, until the proximal end of the implant structure 20 is flush against the lateral wall of the ilium (see also FIGS. 7A and 7B). The guide pin 38 and soft tissue protector are withdrawn, leaving the implant structure 20 residing in the broached passageway, flush with the lateral wall of the ilium (see FIGS. 7A and 7B). In the illustrated embodiment, two additional implant structures 20 are implanted in this manner, as FIG. 6 best shows. In other embodiments, the proximal ends of the implant structures 20 are left proud of the lateral wall of the ilium, such that they extend 1, 2, 3 or 4 mm outside of the ilium. This ensures that the implants 20 engage the hard cortical portion of the ilium rather than just the softer cancellous portion, through which they might migrate if there was no structural support from hard cortical bone. The hard cortical bone can also bear the loads or forces typically exerted on the bone by the implant 20.

The implant structures 20 are sized according to the local anatomy. For the SI-Joint, representative implant structures 20 can range in size, depending upon the local anatomy, from about 35 mm to about 60 mm in length, and about a 7 mm inscribed diameter (i.e. a triangle having a height of about 10.5 mm and a base of about 12 mm). The morphology of the local structures can be generally understood by medical professionals using textbooks of human skeletal anatomy along with their knowledge of the site and its disease or injury. The physician is also able to ascertain the dimensions of the implant structure 20 based upon prior analysis of the morphology of the targeted bone using, for example, plain film x-ray, fluoroscopic x-ray, or MRI or CT scanning.

Using a lateral approach, one or more implant structures 20 can be individually inserted in a minimally invasive fashion across the SI-Joint, as has been described. Conventional tissue access tools, obturators, cannulas, and/or drills can be used for this purpose. Alternatively, the novel tissue access tools described above and in U.S. application Ser. No. 61/609,043, titled "TISSUE DILATOR AND PROTECTER" and filed Mar. 9, 2012, which is hereby incorporated by reference in its entirety, can also be used. No joint preparation, removal of cartilage, or scraping are required before formation of the insertion path or insertion of the implant structures 20, so a minimally invasive insertion path sized approximately at or about the maximum outer diameter of the implant structures 20 can be formed.

The implant structures 20 can obviate the need for autologous bone graft material, additional pedicle screws and/or rods, hollow modular anchorage screws, cannulated compression screws, threaded cages within the joint, or fracture fixation screws. Still, in the physician's discretion, bone graft material and other fixation instrumentation can be used in combination with the implant structures 20.

In a representative procedure, one to six, or perhaps up to eight, implant structures 20 can be used, depending on the size of the patient and the size of the implant structures 20. After installation, the patient would be advised to prevent or reduce loading of the SI-Joint while fusion occurs. This could be about a six to twelve week period or more, depending on the health of the patient and his or her adherence to post-op protocol.

The implant structures 20 make possible surgical techniques that are less invasive than traditional open surgery with no extensive soft tissue stripping. The lateral approach to the SI-Joint provides a straightforward surgical approach that complements the minimally invasive surgical techniques. The profile and design of the implant structures 20 minimize or reduce rotation and micromotion. Rigid implant structures 20 made from titanium provide immediate post-op SI-Joint stability. A bony in-growth region 24 comprising a porous plasma spray coating with irregular surface supports stable bone fixation/fusion. The implant structures 20 and surgical approaches make possible the placement of larger fusion surface areas designed to maximize post-surgical weight bearing capacity and provide a biomechanically rigorous implant designed specifically to stabilize the heavily loaded SI-Joint.

To improve the stability and weight bearing capacity of the implant, the implant can be inserted across three or more cortical walls. For example, after insertion the implant can traverse two cortical walls of the ilium and at least one cortical wall of the sacrum. The cortical bone is much denser and stronger than cancellous bone and can better withstand the large stresses found in the SI-Joint. By crossing three or more cortical walls, the implant can spread the load across more load bearing structures, thereby reducing the amount of load borne by each structure. In addition, movement of the implant within the bone after implantation is reduced by providing structural support in three locations around the implant versus two locations.

In some embodiments, the implant structure can function like a pedicle screw to allow fixation and/or fusion of bone such as the spine and/or SI-Joint. For example, long constructs can be used to join, fuse and/or stabilize a plurality of vertebrae in the thoracic, lumbar, and sacral portions of the spine. For example, to treat spinal disorders such as degenerative scoliosis, the L5 vertebra to the S1 vertebra can be fused using a system of implants and rods as described herein. As illustrated in FIGS. 8A-18E, the implant structure can include a stem portion and a head portion. The stem portion can be formed similarly to the SI-Joint implants described herein and in patent application U.S. Provisional No. 61/642,681, filed May 4, 2012, titled "Fenestrated Implant" and U.S. Pat. No. 8,202,305 titled "Systems and Method for the Fixation or Fusion of Bone." A tulip or saddle structure can be attached to the head portion, and a rod can be inserted into and fixed to a plurality of tulip structures attached to implanted implant structures, thereby fusing and/or stabilizing the spine and/or other bones. In some embodiments, the stem portion, head portion, and tulip or saddle structure can all be cannulated and have a lumen that extends longitudinally through the assembled structure such that the assembled structure can be disposed over a guidewire or guide pin.

Figure 8C:
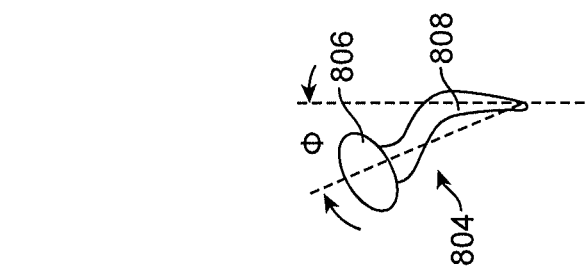
FIGS. 8A to 8C illustrate embodiments of an implant structure with a head portion joined using a Morse taper.
Figure 8B:
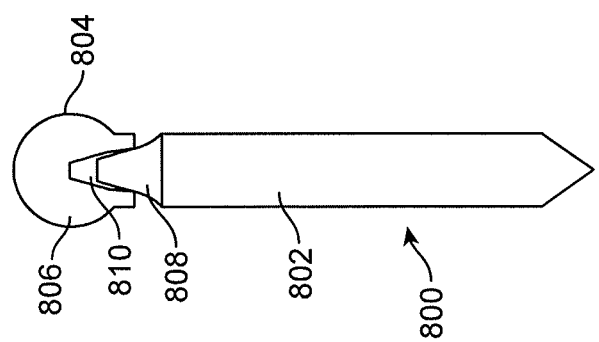
Figure 8A:
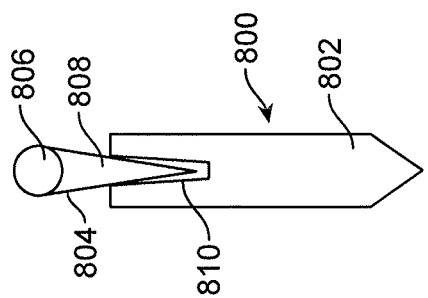

In some embodiments, as illustrated in FIGS. 8A-8C, the head portion 804 can be separate from the stem portion 802. For example, FIGS. 8A-8C illustrate embodiments of the implant structure 800 with a machine taper such as a Morse Taper. In some embodiments as illustrated in FIG. 8A, the head portion 804 can have a ball portion 806 and a tapered shank 808. The tapered shank 808 can fit into a corresponding tapering cavity 810 in the stem portion 802 to form a taper lock that is held together by friction. The length of the tapered shank 808 can be varied, making the distance between the ball portion 806 and proximal end of the stem portion 802 variable.

In some embodiments as illustrated in FIG. 8B, the head portion 804 can have a tapering cavity 810 while the stem portion 802 can have a tapered shank 808 extending from the proximal end of the stem portion 802. The length of the tapered shank 808 can be varied so that the distance between the head portion 804 and stem portion 802 can be adjusted as desired. In some embodiments, the tapered shank 808 of the stem portion 802 can be angled or curved with respect to the longitudinal axis of the stem portion 802. A curved tapered shank 808 can be useful as described below for the embodiment shown in FIG. 8C.

In some embodiments as illustrated in FIG. 8C, the head portion 804 can have a ball portion 806 and a tapered shank 808 that is curved or angled such that the distal portion of the tapered shank 808 is offset or angled with respect to the ball portion 806 and proximal portion of the tapered shank 808. A curved tapered shank 808 can be useful when a suitable implantation location in one or more bones is not aligned with the other implantation locations. In order for the implant structures 800 to line up with the stabilizing rod, a curved tapered shank 808 can be used so that the head portions 806 all line up with the stabilizing rod even if the implantation locations do not line up.

Figure 9:
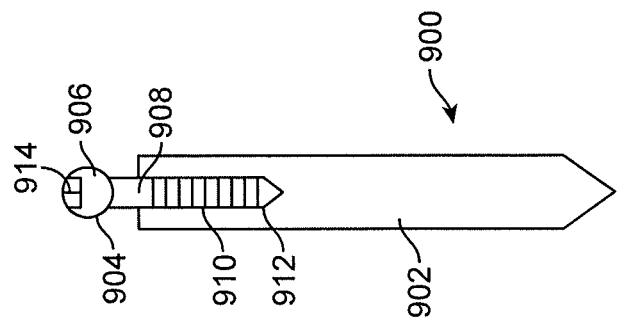
FIG. 9 illustrates an embodiment of an implant structure with a head portion joined using a screw type attachment.

FIG. 9 illustrates another embodiment of an implant structure 900 with a stem portion 902 and a head portion 904. The head portion 904 can have a ball portion 906 and a shank 908. The shank 908 can have threads 910, like a screw, that can be screwed into a cavity 912 with complementary internal threads. The ball portion 904 can have a screw drive 914 that facilitates turning of the head portion 904. The screw drive 914 can be a slot, socket (square, hex, star, etc.), or other typical screw drive 914 mechanism.

FIGS. 10A and 10B illustrate embodiments of integrated implant structures 1000 having a stem portion 1002 and a head portion 1004 that is integral with the stem portion 1002. As shown in FIGS. 10A and 10B, the head portion 1004 is integral or fixed to the stem portion 1002, and therefore the head portion 1004 has a fixed length relative to the stem portion 1002. As shown in FIG. 10A, the head portion 1004 can have a ball portion 1006 that can be attached to a tulip portion that is described in further detail below in, for example, FIGS. 13A and 18A-18C. Alternatively, as shown in FIG. 10B, the head portion 1004 can have a tulip portion 1007 integrated directly with the stem portion 1002. Having an integrated implant structure 1000 can be useful when it is known in advance that an implant structure 1000 will be used in, for example, a fixation or stabilization procedure that requires the use of an implant structure with a head portion 1004. The integrated implant 1000 can reduce procedure time by not requiring the attachment of the head portion 1004 onto the stem portion 1002. In addition, because the head portion 1004 is integral with the stem portion 1002, the integrated implant 1000 may have a greater structural integrity or strength than an implant assembled from separate pieces.

In some embodiments that may be particularly suited for pedicle screw salvage as illustrated in FIGS. 11A and 11B, the implant structure 1100 can have a stem portion 1102 with ledges or fenestrations 1003 that promote bone ingrowth. Examples of fenestrations that can be incorporated into the implant structure 1100 are described in patent application U.S. Provisional No. 61/642,681, filed May 4, 2012, titled "Fenestrated Implant." In some embodiments, the outer surface and/or structure of the stem portion 1102 can be twisted. In some embodiments, the stem portion 1102 may have a round cross-section to better match the cavity within the bone after the old pedicle screw has been removed. In some embodiments, the stem portion 1102 can be tapered. The diameter, shape and profile of the stem portion 1102 can match the bone cavity. In some embodiments, the stem portion 1102 can be oval, round, square, triangular, or rectilinear. In some embodiments, the head portion 1104 can be attached to the stem portion 1102 as described above. For example, the head portion 1104 can be attached to the stem portion 1102 using a Morse taper or screw attachment, or the head portion 1104 can be integral with the stem portion. Pedicle screw salvage can be performed when an implant, such as a pedicle screw, becomes loose within the bone due to windshield wipering or butterflying effects caused by stresses exerted to the bone by the implant. The loose implant can be removed and then replaced by one of the implants described herein.

Figure 12:
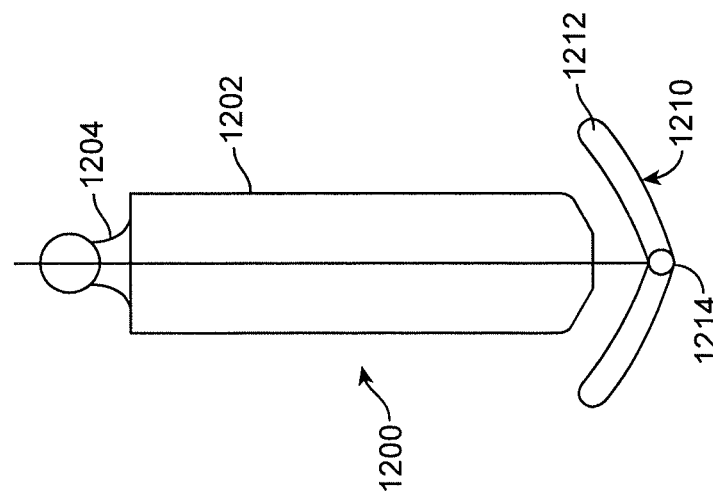
FIG. 12 illustrates an embodiment of an implant structure with an anchor.

FIG. 12 illustrates an implant structure 1200 with a stem portion 1202, a head portion 1204 attached to the proximal end of the stem portion 1202, and an anchor 1210 located distally the distal end of the stem portion 1202. The anchor 1210 can be folded into a collapsed configuration during insertion of the implant structure 1200 into bone, and then unfolded and/or expanded into an expanded configuration after insertion. In some embodiments, the anchor 1210 can have one or more arm portions 1212 that are foldable and/or expandable. In some embodiments, the anchor 1210 can be mechanically actuated from the collapsed configuration to the expanded configuration. In some embodiments, the arm portions 1212 can be joined at a hinge or a hub 1214. In some embodiments, the arm portions 12 can be expanded like the frame of an umbrella. In other embodiments, the anchor 1210 can be self-expanding and can be made of a shape memory material such as a nickel titanium alloy. In some embodiments, the anchor 1210 can be restrained by a sheath or other restraining element when in the collapsed configuration. In some embodiments, the anchor 1210 can be attached to and/or extend from the distal end of the stem portion 1202. The anchor 1210 can reduce or prevent implant structure 1200 migration after implantation.

Figure 13B:
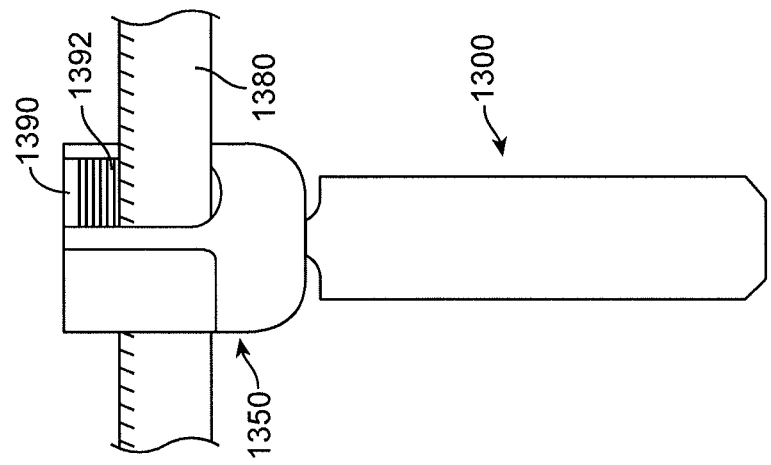
FIGS. 13A and 13B illustrate the attachment of a tulip structure to an implant structure and the securing of a rod to the tulip structure.
Figure 13A:
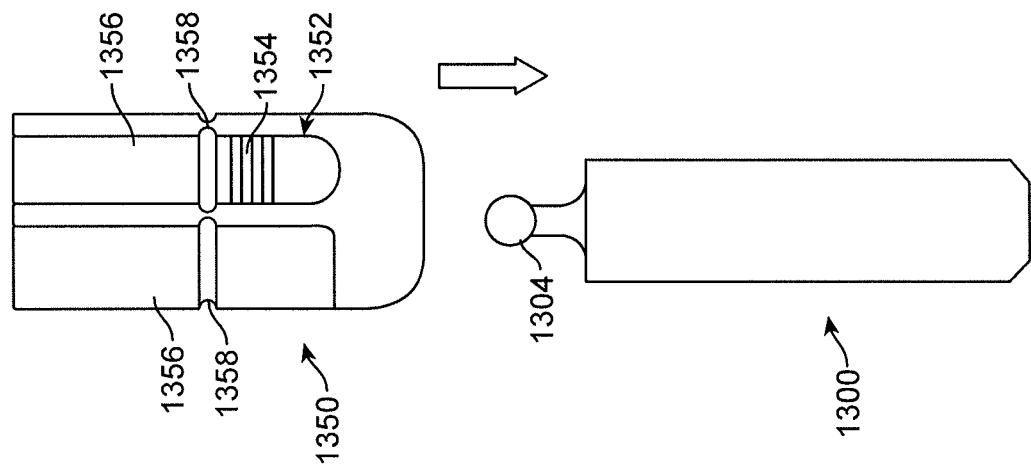

FIGS. 13A and 13B illustrate an implant structure 1300 and a corresponding tulip or saddle structure 1350 that can be attached to the head portion 1304 of the implant structure 1300. The tulip structure 1350 can have a slot 1352 for receiving a rod 1380 that can be used to stabilize the spine. In some embodiments, the tulip structure 1350 can have internal threading 1354 on the two wall portions 1356 that form the slot 1352. In some embodiments, a locking screw 1390 can be used to lock and secure the rod 1380 in place within the tulip structure 1350. The locking screw 1390 can have threading 1392 that correspond to the internal threading 1354 on the two wall portions 1356. To lock and secure the rod in place, the locking screw can simply be screwed in place over the rod 1380. The locking screw 1390 can have a screw drive similar to screw drive 914 described above with respect to FIG. 9. In other embodiments, other fastening mechanisms can be used in place of the locking screw 1390 to hold the rod in place. In some embodiments, the top portions of the wall portions 1356 can be snapped off along a break line 1358. In some embodiments, the break line 1358 can be formed by scoring or thinning the wall portions 1356 along the break line 1358. In some embodiments, the tulip structure 1350 does not have any break lines 1358 or excess wall portions 1356 that can be broken off and can instead have wall portions 1356 that are sized to receive the rod 1380 and locking screw 1390 without having excess material extending past the locking screw 1390.

FIG. 14 illustrates another embodiment of an implant structure 1400 having a stem portion 1402 with a cavity 1412 for receiving an expandable attachment 1410 on the shank 1408 of the head portion 1404. The expandable attachment 1410 on the shank 1408 can have a collapsed configuration and an expanded configuration. The entrance to the cavity 1412 can be a narrowed opening 1414 with a diameter less than the diameter of the cavity 1412. The shank 1408 can be inserted through the narrowed opening 1414 and into the cavity 1412 with the expandable attachment 1410 in the collapsed configuration. Once in the cavity 1412, the expandable attachment 1410 can expand into the expanded configuration, thereby securing the head portion 1404 to the stem portion 1402. The head portion 1404 can have a ball portion 1406 for connected to a tulip structure.

FIG. 15 illustrates another embodiment of a head portion 1504 that can be secured into a cavity 1412 in a stem portion 1402 similar to that illustrated in FIG. 14. The head portion 1504 can have a ball portion 1506 and a shank 1508 with narrowed or undercut portion 1508 and a tapered distal portion 1510. The tapered distal portion 1510 has an end that is narrow enough to be inserted into the narrowed opening 1414. As the tapered distal portion 1510 is further inserted through the narrowed opening 1414, the tapered distal portion 1510 forces the narrowed opening to open wider until the narrowed opening snaps into the undercut portion 1508 of the shank 1508, which in combination with the tapered distal portion 1510 in the cavity, functions to secure the head portion 1504 to the stem portion 1402.

FIG. 16 illustrates another embodiment of a head portion 1604 than can be screwed into an implant structure 1600 in a similar manner as described in connection with FIG. 9, except that in this embodiment, the shank 1608 can have a length that allows the shank 1608 to extend completely through the implant structure 1600. Similarly to the embodiment described in FIG. 9, the shank 1608 can be threaded 1610 and a screw drive on the head portion 1604 can be used to turn the screw like shank 1608. In some embodiments, the threads 1610 on the proximal portion of the shank 1608 can be machine threads for engaging the corresponding threads in the implant structure 1600. The threads 1610 on the distal portion of the shank 1608 can be deeper than the machine threads, which allow the threads to better engage cancellous bone. In some embodiments, the pitch of the threads 1610 can be constant along the length of the shank 1608. In other embodiments, the pitch of the threads 1610 can vary between the different thread types.

FIG. 17 illustrates another embodiment of the attachment of the stem portion 1702 of an implant structure 1700 to a head portion 1704. In this embodiment, the stem portion 1702 has a socket 1708 for receiving a corresponding ball 1706 on the distal end of the head portion 1704. The ball 1706 can reside in the socket 1708 to form a ball and socket joint that permits the head portion 1704 to be rotated through a predetermined angle of rotation. In some embodiments, the angle of rotation can be about 60 degrees or less. In other embodiments, the angle of rotation can be between about 30 to 90 degrees or less.

FIGS. 18A-18E illustrate embodiments of a snap-on tulip or saddle structure 1850. In some embodiments, the tulip structure 1850 can have a slot 1852 for receiving a rod that can be used to stabilize the spine or other bones. In some embodiments, the tulip structure 1850 can have internal threading on the two wall portions 1856 that form the slot 1852. In some embodiments, the wall portions 1856 can have extended tabs that can be snapped off and removed. In some embodiments, the tulip structure 1850 can have a head portion receiving slot 1858 shaped to receive the head portion 1804 attached to the implant structure 1800. The head portion receiving slot 1858 can be located on the distal end of the tulip structure 1850 and provides access to the internal cavity of the tulip structure 1850. The distal end of the tulip structure can have an opening 1860 that allows a portion of the implant structure 1800 to extend through. The diameter or size of the opening 1860 is less than the diameter or size of the head portion 1804, which allows the tulip structure 1850 to receive and then retain the head portion within the cavity of the tulip structure 1850. A stabilizing rod can then be fixed in place within the slot 1852 of the tulip structure 1850, thereby securing the head portion 1804 to the tulip structure 1850.

In some embodiments, the head portion receiving slot 1858 runs up both a portion of one of the side walls and the along the bottom portion to the opening 1860. In some embodiments, the upper portion of the head portion receiving slot 1858 can be circular in shape to accommodate the ball portion of the head portion 1804. The circular portion of the head portion receiving slot 1858 can be located a sufficient distance from the bottom portion of the tulip structure 1850 such that after the ball portion of the head portion 1804 passes into the cavity of the tulip structure 1850, the ball portion drops down against the bottom portion which prevents the ball portion from inadvertently sliding out of the tulip structure 1850. In order for the ball portion of the head portion 1804 to be removed from the tulip structure 1850, the ball portion must be raised from the bottom of the tulip structure 1850 until the ball portion is aligned with the circular portion of the head portion receiving slot 1858, and then the head portion 1804 can be removed from the tulip structure. In some embodiments, the portion of the head portion receiving slot 1858 on the bottom part of the tulip structure can be a straight slot. In other embodiments, the portion of the head portion receiving slot 1858 on the bottom part of the tulip structure can be a curved slot.

The shape and structure of the tulip structure 1850 cavity and opening 1860 allows the tulip structure 1850 to have about a 60 degree angle of movement and rotation after being attached to the head portion 1804. Such a tulip structure 1850 and head portion 1804 can be referred to as polyaxial, meaning the tulip structure 1850 can freely move within a conical area. In other embodiments, the angle of movement and rotation can be between about 30 to 90 degrees or less. Having a substantial angle of movement and rotation allows the implant structure 1800 to be inserted in a wider variety of angles while still allowing the tulip structure 1850 to be aligned with the rod for fixation.

Any of the implants described herein can be used in a variety of surgical procedures, such as stabilization, fixation or fusion of the sacroiliac joint and/or the spine, including vertebra and facet joints. In addition, surgical procedures using a posterior or a posterolateral approach will be particularly suitable for use with the implant structures described herein since the tulip structure of the implant will be aligned with the other implants along the spine after implantation. As described herein, these implant structures can be connected together using a rod that can be secured to each tulip structure. For simplicity, the following procedures will be illustrated and described using a general implant structure 20, but it is understood that any of the implant structures described herein can be used in place of the general implant structure 20.

Figure 19A:
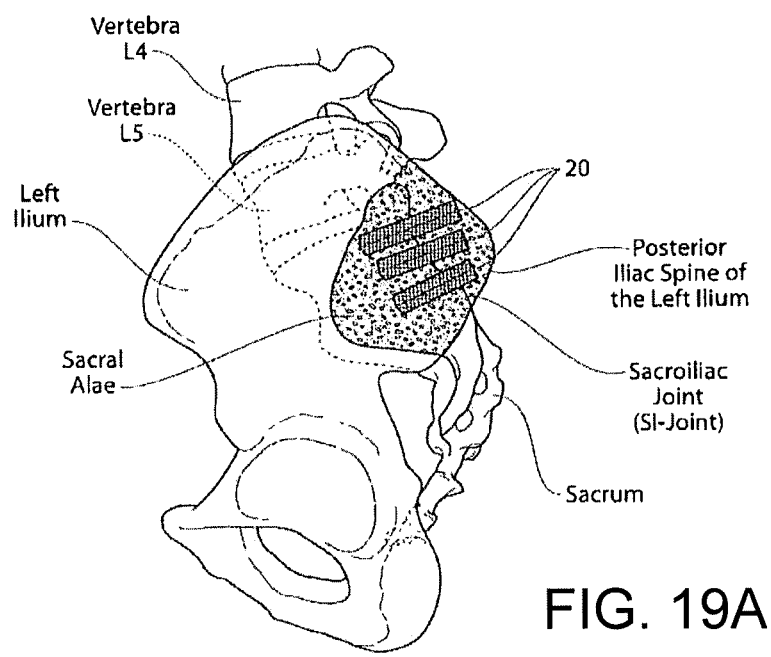
FIGS. 19A and 19B illustrate a lateral view and an axial view of an embodiment of the implant structure crossing the SI-Joint using a posterolateral approach entering from the posterior iliac spine of the ilium, angling through the SI-Joint, and terminating in the sacral alae.
Figure 19B:
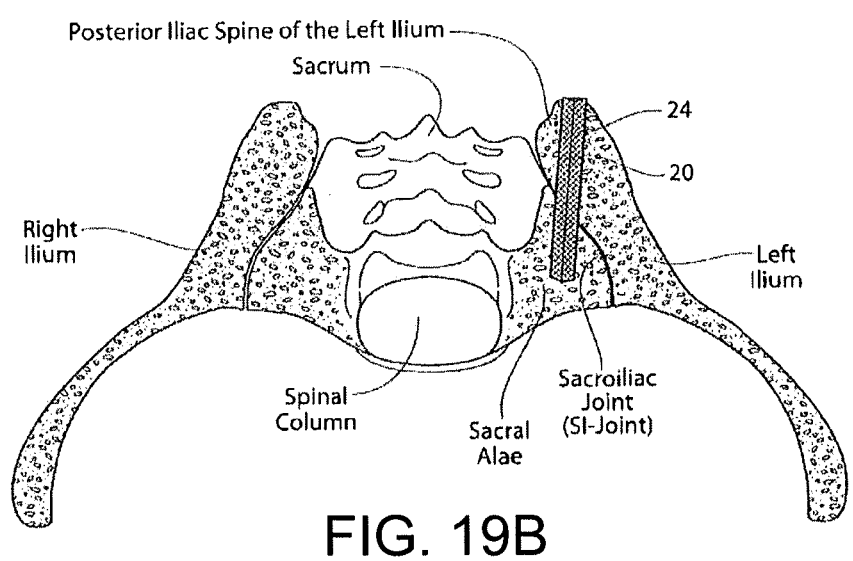

For example, FIGS. 19A and 19B illustrate a lateral view and an axial view of an embodiment of the implant structure crossing the SI-Joint using a posterolateral approach entering from the posterior iliac spine of the ilium, angling through the SI-Joint, and terminating in the sacral alae.

The posterolateral approach involves less soft tissue disruption that the lateral approach, because there is less soft tissue overlying the entry point of the posterior iliac spine of the ilium. Introduction of the implant structure 20 from this region therefore makes possible a smaller, more mobile incision. Further, the implant structure 20 passes through more bone along the posterolateral route than in a strictly lateral route, thereby involving more surface area of the SI-Joint and resulting in more fusion and better fixation of the SI-Joint. Employing the posterolateral approach also makes it possible to bypass all nerve roots, including the L5 nerve root.

The set-up for a posterolateral approach is generally the same as for a lateral approach. It desirably involves the identification of the SI-Joint segments that are to be fixated or fused (arthrodesed) using, e.g., the Faber Test, or CT-guided injection, or X-ray/MRI of SI-Joint. It is desirable performed with the patient lying in a prone position (on their stomach) and is aided by lateral and anterior-posterior (A-P) c-arms. The same surgical tools are used to form the pilot bore 42 over a guide pin 38, except the path of the pilot bore 42 now starts from the posterior iliac spine of the ilium, angles through the SI-Joint, and terminates in the sacral alae. The pilot bore 42 is shaped into the desired profile using a broach, as before described, and the implant structure 20 is inserted into the broached bore 48. The implant structure 20 is tapped through the soft tissue protector over the guide pin 38 from the posterior iliac spine of the ilium, angling through the SI-Joint, and terminating in the sacral alae, until the proximal end of the implant structure 20 is flush against the posterior iliac spine of the ilium. Because of the anatomic morphology of the bone along the posterolateral route, it may be advisable to introduce implant structures of difference sizes, with the most superior being the longest in length, and the others being smaller in length.

Figure 20A:
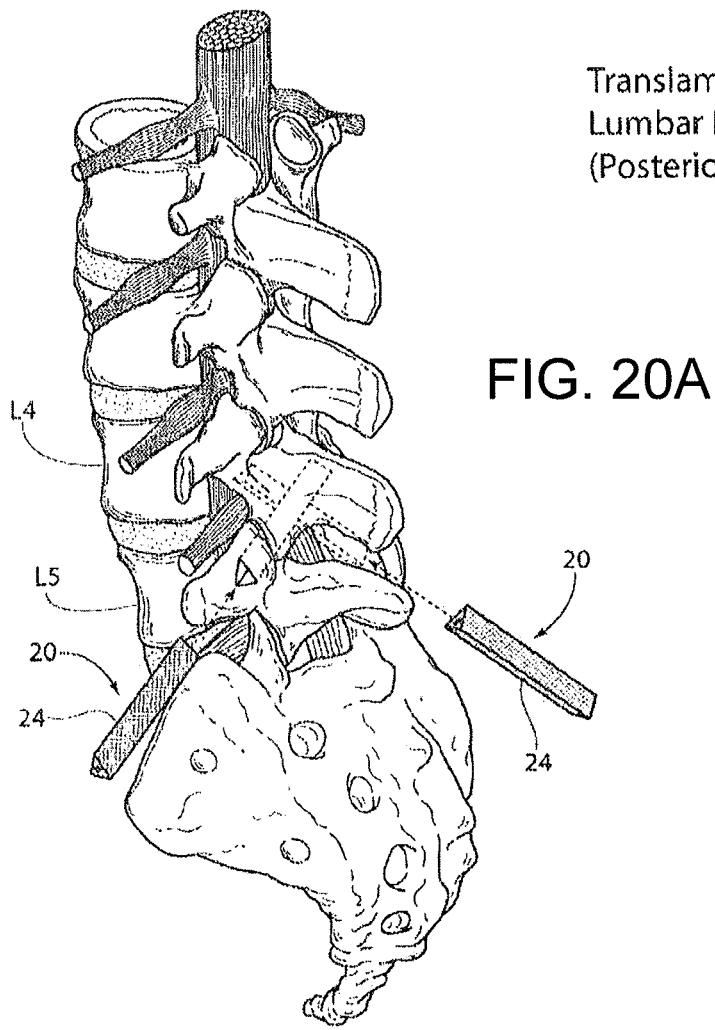
FIG. 20A is an anatomic posterior perspective view, exploded prior to implantation, of a representative configuration of an assembly of one or more implant structures, sized and configured to achieve translaminar lumbar fusion in a non-invasive manner and without removal of the intervertebral disc.
Figure 20B:
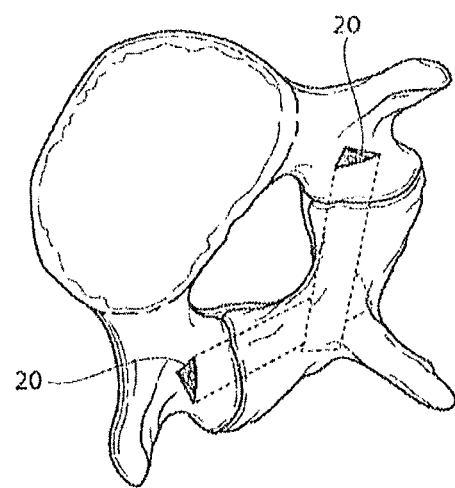
FIG. 20B is an anatomic inferior transverse plane view showing the assembly shown in FIG. 20A after implantation.

FIG. 20A shows, in an exploded view prior to implantation, a representative configuration of an assembly of one or more implant structures 20 sized and configured to achieve translaminar lumbar fusion in a non-invasive manner and without removal of the intervertebral disc. FIG. 20B shows the assembly after implantation, respectively, in an inferior transverse plane view.

As can be seen in the representative embodiment illustrated in FIGS. 20A and 20B, the assembly comprises two implant structures 20. The first implant structure 20 extends from the left superior articular process of vertebra L5, through the adjoining facet capsule into the left inferior articular process of vertebra L4, and, from there, further through the lamina of vertebra L4 into an interior right posterolateral region of vertebra L4 adjacent the spinous process. The second implant structure 20 extends from the right superior articular process of vertebra L5, through the adjoining facet capsule into the right inferior articular process of vertebra L4, and, from there, further through the lamina of vertebra L4 into an interior left posterolateral region of vertebra L4 adjacent the spinous process. The first and second implant structures 20 cross each other within the medial lamina of vertebra L4.

The first and second implant structures 20 are sized and configured according to the local anatomy. The selection of a translaminar lumbar fusion (posterior approach) is indicated when the facet joints are aligned with the sagittal plane. Removal of the intervertebral disc is not required, unless the condition of the disc warrants its removal.

A posterior procedure for implanting the assembly of implant structures 20 shown in FIGS. 20A and 20B comprises (i) identifying the vertebrae of the lumbar spine region that are to be fused; (ii) opening an incision, which comprises, e.g., with the patient lying in a prone position (on their stomach), making a 3 mm posterior incision; and (iii) using a guide pin to establish a desired implantation path through bone for the first (e.g., left side) implant structure 20, which, in FIGS. 20A and 20B, traverses through the left superior articular process of vertebra L5, through the adjoining facet capsule into the left inferior articular process of vertebra L4, and then through the lamina of vertebra L4 into an interior right posterolateral region of vertebra L4 adjacent the spinous process. The method further includes (iv) guided by the guide pin, increasing the cross section of the path; (v) guided by the guide pin, shaping the cross section of the path to correspond with the cross section of the implant structure; (vi) inserting the implant structure 20 through the path over the guide pin; (vii) withdrawing the guide pin; and (viii) using a guide pin to established a desired implantation path through bone for the second (e.g., right side) implant structure 20, which, in FIGS. 20A and 20B, traverses through the right superior articular process of vertebra L5, through the adjoining facet capsule into the right inferior articular process of vertebra L4, and through the lamina of vertebra L4 into an interior left posterolateral region of vertebra L4 adjacent the spinous process. The physician repeats the remainder of the above-described procedure sequentially for the right implant structure 20 as for the left, and, after withdrawing the guide pin, closes the incision.

The intimate contact created between the bony in-growth or through-growth region 24 along the surface of the implant structure 20 across the facet joint accelerates bony in-growth or through-growth onto, into, or through the implant structure 20, to accelerate fusion of the facets joints between L4 and L5. Of course, translaminar lumbar fusion between L5 and S1 can be achieved using first and second implant structures in the same manner.

Figure 21A:
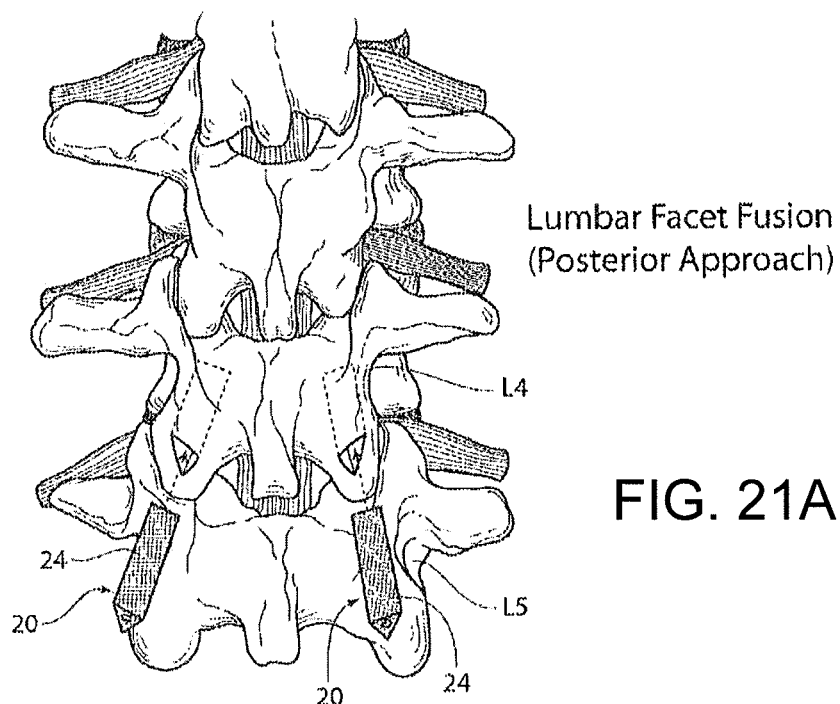
FIG. 21A is an anatomic posterior perspective view, exploded prior to implantation, of a representative configuration of an assembly of one or more implant structures, sized and configured to achieve lumbar facet fusion, in a non-invasive manner.
Figure 21B:
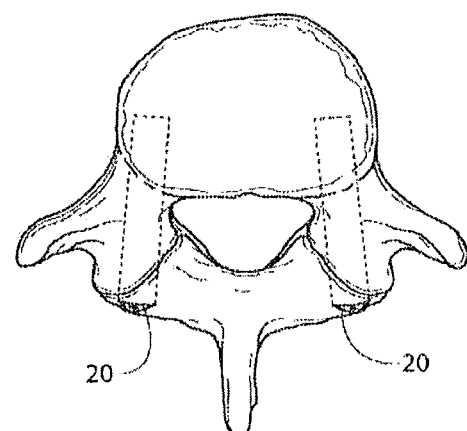
FIG. 21B is an anatomic inferior transverse plane view showing the assembly shown in FIG. 21A after implantation.
Figure 21C:
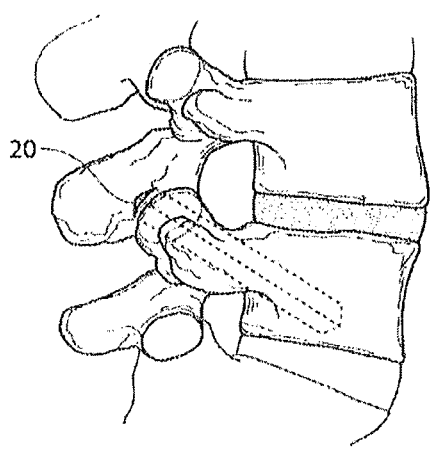
FIG. 21C is an anatomic lateral view showing the assembly shown in FIG. 21A after implantation.

FIG. 21A shows, in an exploded view prior to implantation, a representative configuration of an assembly of one or more implant structures 20 sized and configured to lumbar facet fusion, in a non-invasive manner and without removal of the intervertebral disc. FIGS. 21B and 21C show the assembly after implantation, respectively, in an inferior transverse plane view and a lateral view.

As can be seen in the representative embodiment illustrated in FIGS. 21A to 21C, the assembly comprises two implant structures 20. The first implant structure 20 extends from the left inferior articular process of vertebra L4, through the adjoining facet capsule into the left superior articular process of vertebra L5 and into the pedicle of vertebra L5. The second implant structure 20 extends from the right inferior articular process of vertebra L5, through the adjoining facet capsule into the right superior articular process of vertebra L5 and into the pedicle of vertebra L5. In this arrangement, the first and second implant structures 20 extend in parallel directions on the left and right pedicles of vertebra L5. The first and second implant structures 20 are sized and configured according to the local anatomy. The selection of lumbar facet fusion (posterior approach) is indicated when the facet joints are coronally angled. Removal of the intervertebral disc is not necessary, unless the condition of the disc warrants its removal.

A posterior procedure for implanting the assembly of implant structures 20 shown in FIGS. 21A to 21C comprises (i) identifying the vertebrae of the lumbar spine region that are to be fused; (ii) opening an incision, which comprises, e.g., with the patient lying in a prone position (on their stomach), making a 3 mm posterior incision; and (iii) using a guide pin to established a desired implantation path through bone for the first (e.g., left side) implant structure 20, which, in FIGS. 21A to 21C, traverses through the left inferior articular process of vertebra L4, through the adjoining facet capsule into the left superior articular process of vertebra L5 and into the pedicle of vertebra L5. The method further includes (iv) guided by the guide pin, increasing the cross section of the path; (v) guided by the guide pin, shaping the cross section of the path to correspond with the cross section of the implant structure 20; (vi) inserting the implant structure 20 through the path over the guide pin; (vii) withdrawing the guide pin; and (viii) using a guide pin to establish a desired implantation path through bone for the second (e.g., right side) implant structure 20, which, in FIGS. 21A to 21C, traverses through the right inferior articular process of vertebra L4, through the adjoining facet capsule into the right superior articular process of vertebra L5 and into the pedicle of vertebra L5. The physician repeats the remainder of the above-described procedure sequentially for the right implant structure 20 as for the left and, withdrawing the guide pin, closes the incision.

The intimate contact created between the bony in-growth or through-growth region 24 along the surface of the implant structure 20 across the facet joint accelerates bony in-growth or through-growth onto, into, or through the implant structure 20, to accelerate fusion of the facets joints between L4 and L5.

Of course, transfacet lumbar fusion between L5 and S1 can be achieved using first and second implant structures in the same manner.

Figure 22A:
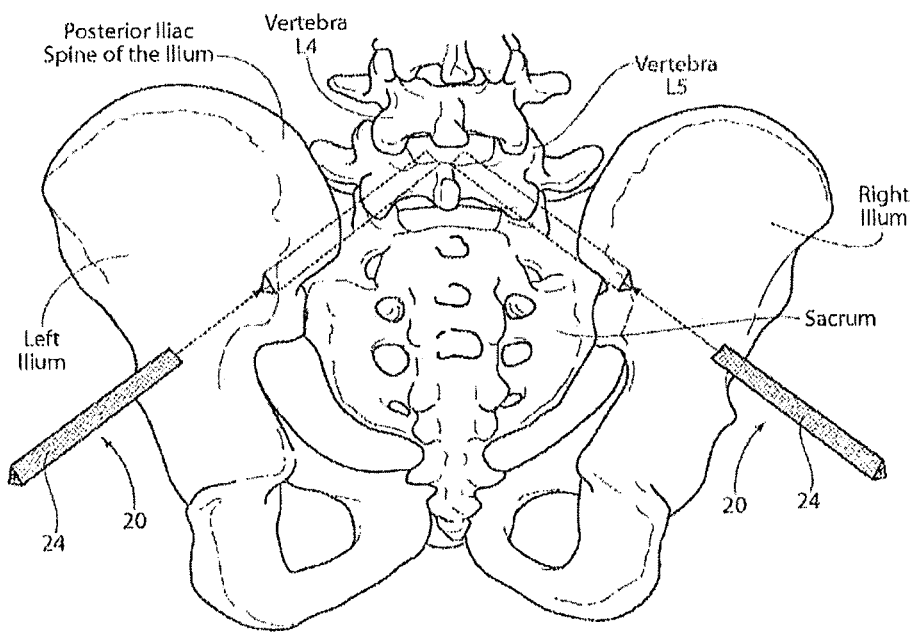
FIG. 22A is an anatomic posterior view showing, in an exploded view prior to implantation, another representative configuration of an assembly of one or more implant structures sized and configured to achieve fusion between lumbar vertebra L5 and sacral vertebra S1, in a non-invasive manner and without removal of the intervertebral disc, using a posterolateral approach entering from the posterior iliac spine of the ilium, angling through the SI-Joint, and terminating in the lumbar vertebra L5.
Figure 22B:
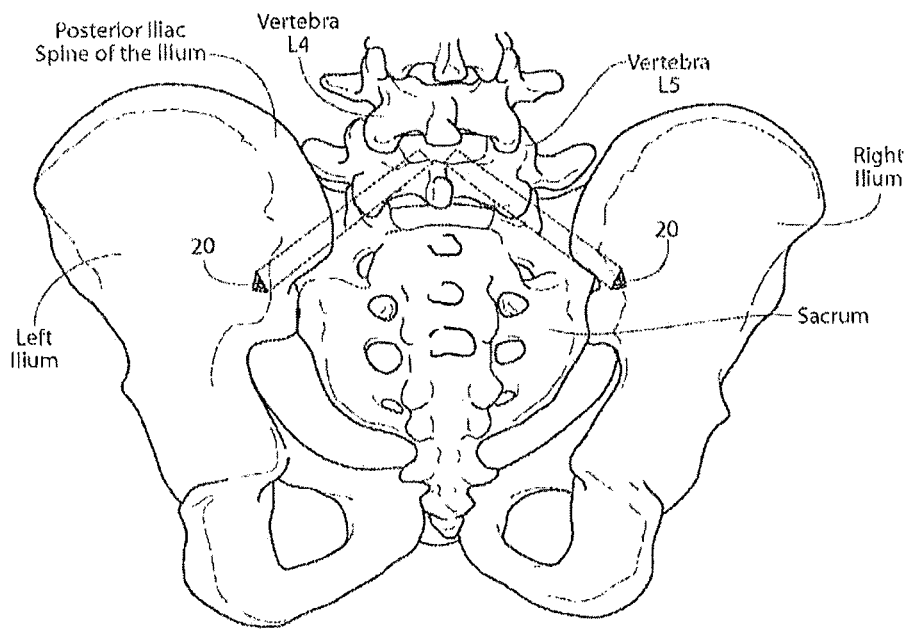
FIG. 22B is an anatomic posterior view showing the assembly shown in FIG. 22A after implantation.

FIG. 22A shows, in an exploded view prior to implantation, another representative configuration of an assembly of one or more implant structures 20 sized and configured to achieve fusion between lumbar vertebra L5 and sacral vertebra S1, in a non-invasive manner and without removal of the intervertebral disc. FIGS. 22B and 22C show the assembly after implantation.

As FIGS. 22A and 22B show, the one or more implant structures are introduced in a posterolateral approach entering from the posterior iliac spine of the ilium, angling through the SI-Joint into and through the sacral vertebra S1, and terminating in the lumbar vertebra L5. This path and resulting placement of the implant structures 20 are also shown in FIG. 22C. In the illustrated embodiment, two implant structures 20 are placed in this manner, but there can be more or fewer implant structures 20. Also in the illustrated embodiment, the implant structures 20 are triangular in cross section, but it should be appreciated that implant structures 20 of other cross sections as previously described can be used.

The posterolateral approach involves less soft tissue disruption than the lateral approach, because there is less soft tissue overlying the entry point of the posterior iliac spine of the ilium. Introduction of the implant structure 20 from this region therefore makes possible a smaller, more mobile incision.

The set-up for a posterolateral approach is generally the same as for a lateral approach. It desirably involves the identification of the lumbar region that is to be fixated or fused (arthrodesed) using, e.g., the Faber Test, or CT-guided injection, or X-ray/MRI of the L5-S1 level. It is desirable performed with the patient lying in a prone position (on their stomach) and is aided by lateral and anterior-posterior (A-P) c-arms. The same surgical tools are used to form the pilot bore over a guide pin (e.g., on the right side), except the path of the pilot bore now starts from the posterior iliac spine of the ilium, angles through the SI-Joint, and terminates in the lumbar vertebra L5. The broached bore is formed, and the right implant 20 structure is inserted. The guide pin is withdrawn, and the procedure is repeated for the left implant structure 20, or vice versa. The incision site(s) are closed.

The assembly as described makes possible the achievement of trans-iliac lumbar fusion using a posterolateral approach in a non-invasive manner, with minimal incision, and without necessarily removing the intervertebral disc between L5 and S1.

Figure 23A:
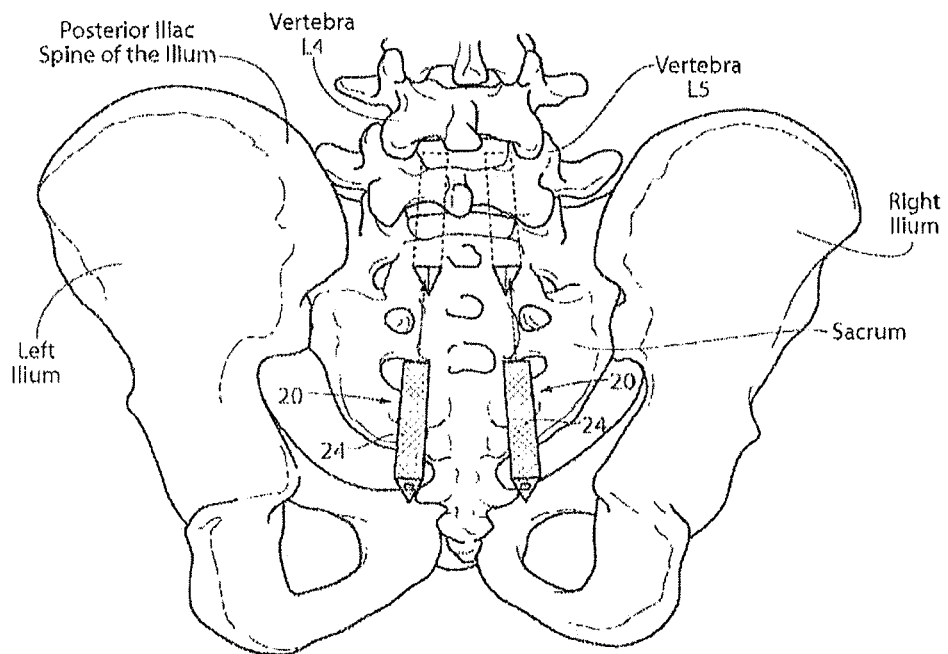
FIG. 23A is an anatomic anterior perspective view showing, in an exploded view prior to implantation, a representative configuration of an assembly of one or more implant structures, sized and configured to stabilize a spondylolisthesis at the L5/S1 articulation.
Figure 23B:
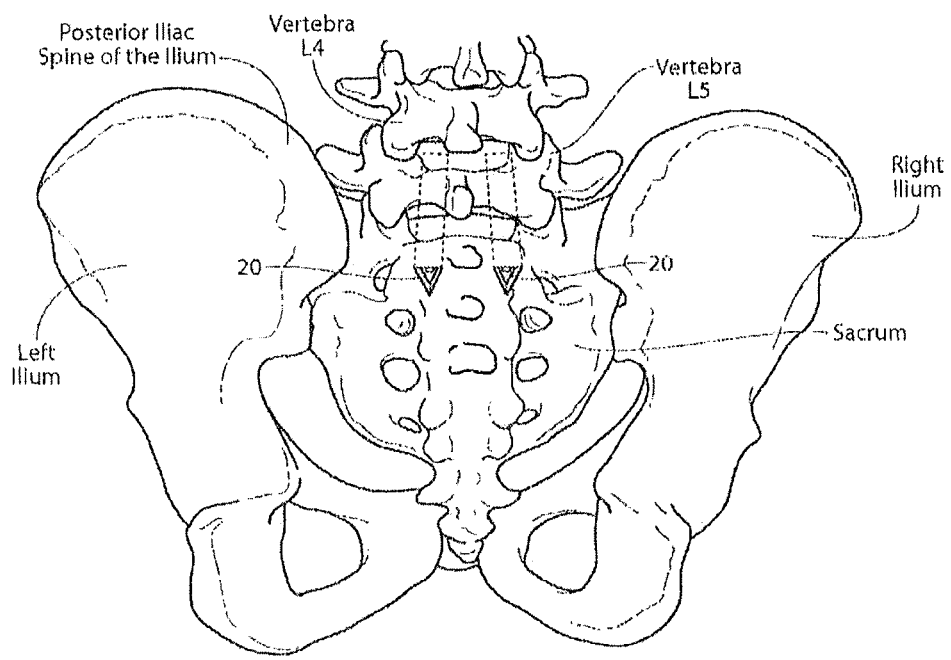
FIG. 23B is an anatomic anterior perspective view showing the assembly shown in FIG. 23A after implantation.
Figure 23C:
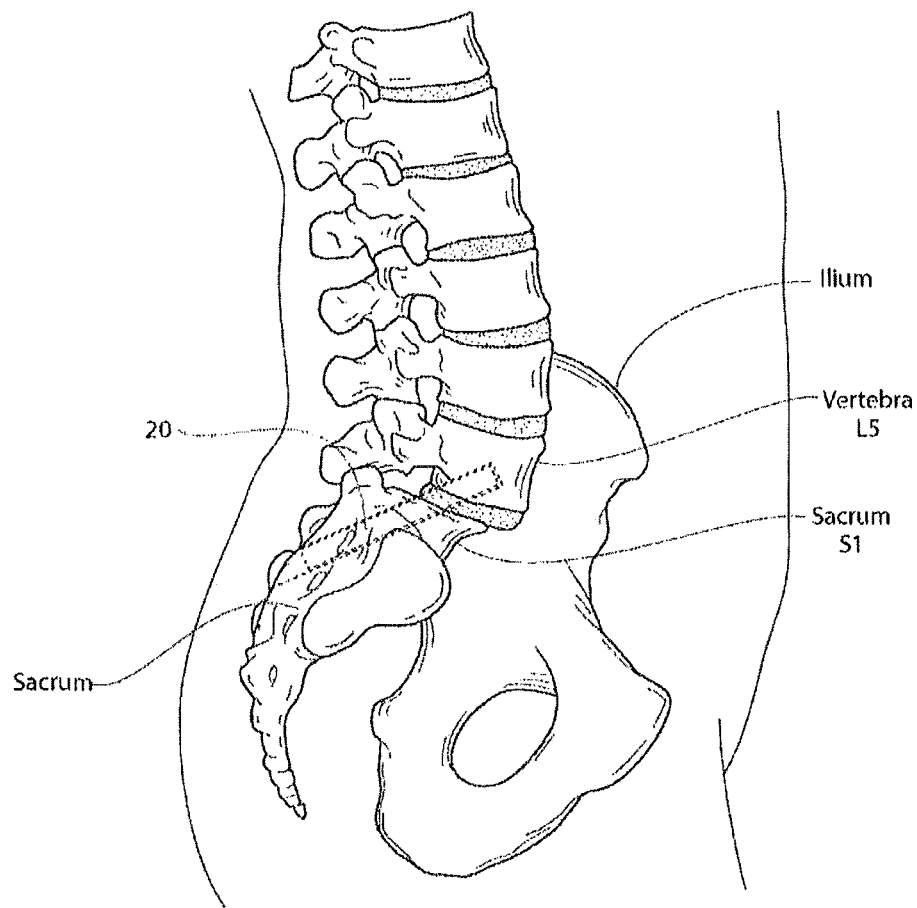
FIG. 23C is an anatomic lateral view showing the assembly shown in FIG. 23B.

FIG. 23A shows, in an exploded view prior to implantation, a representative configuration of an assembly of one or more implant structures 20 sized and configured to stabilize the spondylolisthesis at the L5/S1 articulation. FIGS. 23B and 23C show the assembly after implantation.

As shown, the implant structure 20 extends from a posterolateral region of the sacral vertebra S1, across the intervertebral disc into an opposite anterolateral region of the lumbar vertebra L5. The implant structure 20 extends in an angled path (e.g., about 20 degrees to about 40 degrees off horizontal) through the sacral vertebra S1 in a superior direction, through the adjoining intervertebral disc, and terminates in the lumbar vertebra L5.

A physician can employ a posterior approach for implanting the implant structure 20 shown in FIGS. 23A, 23B, and 23C, which includes forming a pilot bore over a guide pin inserted in the angled path from the posterior of the sacral vertebra S1 through the intervertebral disc and into an opposite anterolateral region of the lumbar vertebra L5, forming a broached bore, inserting the implant structure 20, and withdrawing the guide pin. The incision site is then closed. As previously described, more than one implant structure 20 can be placed in the same manner to stabilize a spondylolisthesis.

The physician can, if desired, combine stabilization of the spondylolisthesis, as shown in FIG. 23A/B/C, with a reduction, realigning L5 and S-1. The physician can also, if desired, combine stabilization of the spondylolisthesis, as shown in FIG. 23A/B/C (with or without reduction of the spondylolisthesis), with a lumbar facet fusion, as shown in FIGS. 21A to 21C. The physician can also, if desired, combine stabilization of the spondylolisthesis, as shown in FIG. 23A/B/C, with a decompression, e.g., by the posterior removal of the spinous process and laminae bilaterally.

Figure 24:
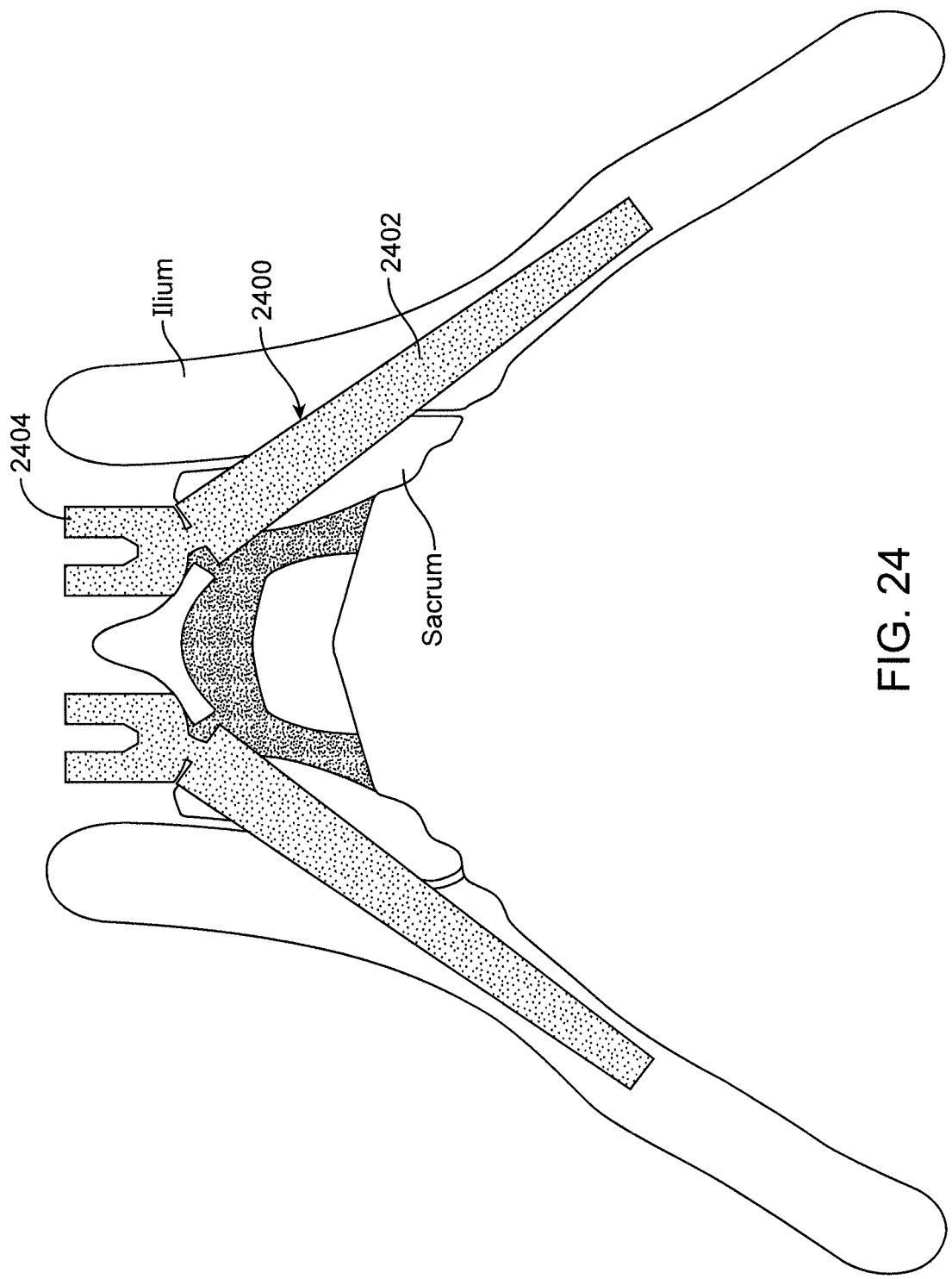
FIG. 24 is an axial view illustrating an implant inserted through a posteromedial approach.

In addition, in some embodiments as shown in FIG. 24, a posteromedial approach can be used to insert the implant 2400. For example, the implant 2400 can be inserted through the posterolateral sacrum, across the alae, through the SI-Joint, and into the ilium where the implant may terminate. As illustrated, the implant 2400 can have a stem portion 2402 that is inserted into the bone and a tulip portion 2404 that remains outside the bone.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiment whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A system for fusing or stabilizing a plurality of bones, the system comprising:
an implant structure having a stem portion and a head portion, the head portion including a shank that has a length such that it extends through the stem portion and distally from the stem portion, the implant structure having a linear longitudinal axis extending along the stem portion and the head portion, the stem portion having a rectilinear cross sectional area transverse to the linear longitudinal axis,
the shank having a distal region with external threads that are shaped to interface with corresponding internal threads on the stem portion,
the stem portion having a length and a configuration such that it can be stably implanted into and through a sacrum, across a sacroiliac joint, and into an ilium;
a tulip or saddle structure attached to the head portion, a proximal end of the head portion spaced from a distal end of the shank portion at a distance such that the tulip is secured to the proximal end of the head portion when the distal end of the shank is implanted in the ilium; and
a rod secured within the tulip or saddle structure.

2. The system of claim 1, wherein the head portion is connected to the stem portion with a Morse taper.

3. The system of claim 1, wherein the head portion is connected to the stem portion with a screw attachment.

4. The system of claim 1, wherein the head portion is integral with the stem portion.

5. The system of claim 1, wherein the tulip or saddle structure comprises a first slot and a cavity for receiving the head portion.

6. The system of claim 1, wherein the tulip or saddle structure is rotatable through a 60 degree range of motion.

7. An implant for spinal fixation or fusion, the implant comprising:
an elongate body having a stem portion, a head portion, and a linear longitudinal axis, the head portion including a shank with a length such that it extends through the stem portion and distally from the stem portion, the stem portion having a rectilinear cross sectional area transverse to the linear longitudinal axis,
the shank having a distal region with external threads that are shaped to interface with corresponding internal threads on the stem portion,
the stem portion having a length and a configuration such that it can be stably implanted into and through a sacrum, across a sacroiliac joint, and into an ilium; and
a tulip or saddle structure attached to the head portion,
a proximal end of the head portion spaced from a distal end of the shank portion at a distance such that the tulip is secured to the head portion when the distal end of the shank is implanted in the ilium.

8. The implant of claim 7, wherein the head portion is connected to the stem portion with a Morse taper.

9. The implant of claim 7, wherein the head portion is connected to the stem portion with a screw attachment.

10. The implant of claim 9, wherein the screw attachment is formed on a shank that extends through the entire length of the stem portion.

11. The implant of claim 7, wherein the head portion is integral with the stem portion.

12. The implant of claim 7, wherein the tulip or saddle structure comprises a first slot and a cavity for receiving the head portion.

13. The implant of claim 7, wherein the tulip or saddle structure is rotatable through a 60 degree range of motion.

14. The implant of claim 7, wherein the head portion is connected to the stem portion through an expandable attachment on the head portion that is secured within a cavity in the stem portion.

15. The implant of claim 7, wherein the tulip or saddle structure is attached to the head portion through a snap on connection comprising a slot in the tulip or saddle structure for receiving the head portion.

16. An implant for spinal fixation or fusion, the implant comprising:
   a stem portion, a head portion, and a linear longitudinal axis, the head portion including a shank with a length such that it extends through the stem portion and distally from the stem portion, the stem portion having a rectilinear cross sectional area transverse to the linear longitudinal axis,
   the shank having a distal region with external threads that are shaped to interface with corresponding internal threads on the stem portion,
   the implant having a length and a configuration such that the stem extends in a sacrum and across a sacroiliac joint when the implant is implanted within the sacrum, across the sacroiliac joint, and into an ilium.

17. The implant of claim 16, further comprising a tulip or saddle secured or securable to a proximal end region of the head portion, the implant having a length such that the tulip or saddle is disposed outside of the sacrum when a distal end of the shank is in the ilium.

18. The implant of claim 17, further comprising a rod that is sized and shaped to be secured to the tulip or saddle when the distal end of the shank is in the ilium.

19. The implant of claim 16, wherein the implant includes a proximal region with external threads.

20. The implant of claim 16, wherein the stem portion has a triangular cross sectional area transverse to the linear longitudinal axis.

* * * * *